United States Patent [19]

Gurtiss, III

[11] Patent Number: 5,389,368
[45] Date of Patent: *Feb. 14, 1995

[54] AVIRULENT MICROBES AND USES THEREFOR

[75] Inventor: Roy Gurtiss, III, St. Louis, Mo.

[73] Assignee: Washington University, St. Louis, Mo.

[*] Notice: The portion of the term of this patent subsequent to Mar. 15, 2011 has been disclaimed.

[21] Appl. No.: 965,607

[22] Filed: Oct. 22, 1992

Related U.S. Application Data

[63] Continuation of Ser. No. 200,934, Jun. 1, 1988, abandoned, which is a continuation-in-part of Ser. No. 58,360, Jun. 4, 1987, abandoned.

[51] Int. Cl.⁶ .................. A61K 39/112; A61K 39/108
[52] U.S. Cl. ............................ 424/93.2; 424/93.4; 424/93.1; 435/320.1; 435/172.3; 935/72; 935/73
[58] Field of Search .............. 424/92, 93 A, 93 D, 424/93 P; 435/252.3, 252.33, 879, 320.1; 935/65

[56] References Cited

U.S. PATENT DOCUMENTS

| | | | |
|---|---|---|---|
| 3,931,398 | 1/1976 | Gaffer et al. | 424/92 |
| 3,975,517 | 8/1976 | Wilson | 424/87 |
| 4,203,971 | 5/1980 | Buchanan | 424/92 |
| 4,250,262 | 2/1981 | Taubman et al. | 435/193 |
| 4,550,081 | 10/1985 | Stocker | 435/252.3 |
| 4,888,170 | 12/1989 | Curtiss, III | 424/93 R |

OTHER PUBLICATIONS

DiBacco, T. V. 1993, "Backer of Herbal Remedies Fought Medical Establishment–Patented 'Cures' were sold to Families" in: Washington Post Health/Sep. 14, 1993.
Nossal, G. J. V., Sir. 1993. Scientic American 269(3), 53–62.
Nnalue et al., *Microbial Pathogenesis* (1989) 7:299–310.
Curtiss, III, et al., *Immunological Investigations* (1989) 18(1-4):583–596.
Nakamura et al., *Japan Journal of Veterinary Science* (1988) 50:606–713.
Nnalue et al., *Infection and Immunity* (1987) 55(4):955–962.
British Journal of Experimenting Pathology 32:85–96, (1951). G. A. Bacon et al.
Journal of Bacteriology 103:513–516, (1970). T. Yokota et al.
Infection and Immunity 4:663–673, (1971). R. Germanier et al.
The Journal of Experimental Medicine 139:1189–1203, (1974). P. B. Carter et al.
Molecular and General Genetics 142:289–298, (1975). Y. Komeda et al.
The Journal of Infectious Diseases 131:553–558, (1975). R. Germanier et al.
Journal of Bacteriology 134:356–358, (1978). M. H. Saier, Jr. et al.
Infection and Immunity 22:763–770, (1978). A. W. Hohmann et al.
Journal of Bacteriology 141:751–757, (1980). B. J. Scholte et al.
Infection and Immunity 34:746–750, (1981). S. B. Formal et al.

(List continued on next page.)

*Primary Examiner*—Christopher S. F. Low
*Attorney, Agent, or Firm*—Rogers, Howell & Haferkamp

[57] ABSTRACT

This invention provides a vaccine for the immunization of a vertebrate or invertebrate comprising an avirulent derivative of a pathogenic microbe said derivative being substantially incapable of producing functional adenylate cyclase and cyclic AMP receptor protein. The invention also provides a vaccine for the immunization of a vertebrate and invertebrate comprising a virulent derivative of a pathogenic microbe said derivative being substantially incapable of producing functional adenylate cyclase and cyclic AMP receptor protein while being capable of expressing a recombinant gene derived from a pathogen of said vertebrate to produce and antigen capable of inducing an immune response in said vertebrate against said pathogen.

11 Claims, 8 Drawing Sheets

OTHER PUBLICATIONS

Molecular and General Genetics 182:480–489, (1981). T. Melton et al.

Annual Microbiology 135A:389–398, (1981). M. Y. Popoff et al.

Infection and Immunity 50:586–587, (1985). M. Nakamura et al.

FEMS Microbiology Letters 28:317–321, (1985). G. Stevenson et al.

Cell 41:745–751, (1985). S. Garges et al.

Infection and Immunity 53:685–692, (1986). J. D. Clements et al.

Journal of Dental Research 65:1034–1045, (1986). R. Curtiss III.

Curtiss et al. 1987. Infection and Immunity 55, 3035–3043.

AVIRULENT MICROBES AND USES THEREFOR

CROSS-REFERENCE TO RELATED APPLICATION

This application is a continuation of application Ser. No. 07/200,934, filed Jun. 1, 1988, now abandoned which is a CIP of 07/058,360, filed Jun. 4, 1987, now abandoned.

FIELD OF THE INVENTION

This invention relates to avirulent microbes, their method of preparation, and their use in vaccines.

BACKGROUND OF THE INVENTION

Previously used vaccines against infectious diseases have generally comprised (I) specific components purified from the etiologic agents, including intact antigens, fragments thereof, or synthetic analogs of naturally occurring antigens or epitopes, (II) antiidiotypic antibodies, (III) the whole killed etiologic agent, or (IV) an avirulent derivative of the etiologic agent as a live vaccine. Numerous vaccines of these types exist, of which the following are selected examples:

U.S. Pat. No. 4,250,262 discloses methods for recovering the enzyme glucosyltransferase from *Streptococcus mutans* and the use of this purified enzyme in local immunization against dental caries, a Type I vaccine. Details for culturing the bacteria, purifying the enzyme, and using the enzyme to stimulate IgA antibody in saliva are presented for serotype a, c or g of *S. mutans*. Other examples of vaccines from purified specific components of bacteria are found in U.S. Pat. Nos. 4,203,971 and 3,239,749, which disclose a vaccine useful against infection by *Neisseria gonnorrhoeae* which consists of a glycoprotein from the outer coat material of gonococci. Injection of the glycoprotein stimulates a bactericidal antibody.

The use of dead *S. mutans* cells to immunize against tooth decay via administering in the mouth, which is disclosed in U.S. Pat. No. 3,931,398, is an example of a Type III vaccine. The inventors recognized that immunoglobulin A (IgA) antibodies were the antibodies being produced and that they resulted in a decrease in plaque formation.

A live bacterial vaccine (Type IV) which contains selected strains of *Escherichia coli* bacteria is disclosed in U.S. Pat. No. 3,975,517. The bacteria were treated with dilute formalin to attenuate or partially inactivate them before injection into the mammary gland of a sow. Antibody thereby produced was later found in the milk and protected newborn swine against *E. coli* infections. The formalin treatment that caused the *E. coli* inactivation was only a temporary attenuation of the bacteria and care had to be taken to prevent bacterial recovery before injection. Such recovery would have resulted in serious infection rather than protection.

It has been possible to develop avirulent strains by the introduction of mutations into said strains which results in the strains being substantially incapable of survival in a host. These strains can be said to be genetically attenuated. For ease of description the principles of genetic attenuation will be illustrated by reference to the Salmonella system, however, the principles are broadly applicable as will be discussed below.

*Salmonella typhimurium*, *S. typhi* and other Salmonella species with invasive properties enter deep tissues after oral ingestion by attaching to, invading and proliferating in the cells of the gut-associated lymphoid tissue (GALT; Peyer's Patches) (Carter and Collins, *J. Exp. Med.* 139: 1189-1203, (1974)). Since Salmonella-mediated delivery of an antigen to the GALT elicits a generalized secretory immune response as well as humoral and cellular immune responses, avirulent Salmonella mutants that have lost the ability to cause disease without impairment in their ability to attach to and invade the GALT are likely to serve as effective vectors to deliver foreign antigens, such as colonization or virulence antigens, to the GALT and to induce protective immunity against the pathogen from which such antigens were derived. The construction of avirulent Salmonella vaccine strains that express antigens from other microorganisms has been accomplished via classical gene transfer procedures (Formal et al., *Infect. Immun.* 34: 746-750, (1981)) as well as by using recombinant DNA technologies. In the latter case, avirulent Salmonella strains have been constructed expressing genes from organisms that normally exchange genetic information with Salmonella (Stevenson and Manning, *FEMS Microbiol. Lett.* 28:317-321 (1985); Clements et al., *Infect. Imm.* 53:685-692, (1986)), as well as from microorganisms that are unable to transfer genetic information to Salmonella by classical means of gene transmission (Curtiss, *J. Dent. Res* 65:1039-1045 (1986)). Such bivalent avirulent Salmonella strains have been shown to elicit antibodies and in one instance a cellular immune response (Brown et al., *J. Infect. Dis.* 155:86-92 (1987)) to the expressed antigen, but data pertaining to induction of protective immunity against the pathogen supplying the colonization or virulence antigen is still scant.

Bacon et al., (*Brit. Exp. Pathol.* 32:85-96, (1951)) were first to investigate the avirulence of auxotrophic mutants of *S. typhi*. They noted that mutants with requirements for purines, p-aminobenzoic acid, and aspartate had reduced virulence for mice. Germanier and Furer, (*Infect. Immun.* 4:663-673, (1971)) first investigated use of gale mutants of *S. typhimurim* for avirulence and immunogenicity in mice and then proposed use of the *S. typhi* gale mutant Ty21a as a vaccine against typhoid fever in humans (*J. Infect. Dis.* 131:553-558 (1975)). Stocker (U.S. Pat. No. 4,550,081) employed transposon mutagenesis with Tn10 followed by selection for fusaric acid resistance that leads to deletional loss of Tn10 and adjacent DNA sequences to yield deletion mutations unable to revert, a problem that was apparent in the mutants used by Bacon et al. Stocker initially isolated aroA deletion ($\Delta$) mutants impaired in the ability to synthesize the aromatic amino acid family of compounds, including p-aminobenzoic acid needed for folate biosynthesis and dihydroxybenzoic acid, a precursor to enterochelin, and more recently combined the $\Delta$aroA mutation with a deletion mutation abolishing adenine biosynthesis. Tn10-induced and fusaric acid resistance-generated $\Delta$asd mutations that impose a requirement for diaminopimelic acid have been employed to render *S. typhimurium* avirulent without impairing its ability to induce a generalized secretory immune response. Since many Salmonella possess a plasmid that contributes to virulence, plasmid-cured derivatives have been investigated and proposed for use as live vaccines (Nakamura et al., Infect. Immun. 50:586-587 (1985)).

Although each of the above described means for rendering Salmonella avirulent without impairing immunogenicity has merit, each has problems. galE mutants are difficult to grow to maintain immunogenicity, since they are galactose-sensitive but must be grown in the presence of galactose to produce normal LPS which, however, selectively leads to galactose-resistant variants that are non-immunogenic. Although ΔaroA mutants abolish the synthesis of both enterochelin and folic acid, the necessity of enterochelin for *S. typhimurium* virulence has been called into question by the extensive results of Benjamin et al. (*Infect. Immun.* 50:392-97, (1985)) that demonstrate that any and all mutations that interfere with *S. typhimurium's* ability to chelate and transport iron are without significant effect on virulence. Therefore the avirulence of ΔaroA mutants is most likely solely due to the inability to synthesize p-aminobenzoic acid (pABA) and therefore folic acid. Since Bacon et al. (supra) observed that administering p-aminobenzoic acid in the diet of mice infected with mutants unable to synthesize pABA led to wild-type levels of virulence, one must be concerned with phenotypic reversal of avirulence in vaccine strains due to dietary consumption of metabolites whose synthesis is blocked in the avirulent mutants. The Δasd mutants, although not having some of these other difficulties, rapidly die following oral feeding and invasion of the GALT, and are thus only effective at eliciting a generalized mucosal immunity and are ineffective in inducing humoral and cellular immunity.

This invention addresses many of the deficiencies of the prior art vaccines by employing transposon-induced mutants in which the impairment leading to avirulence can not be repaired by diet or by anything the animal host could supply. These deletions could, of course, be introduced by recombinant DNA techniques.

BRIEF DESCRIPTION OF THE INVENTION

This invention provides a vaccine for the immunization of a vertebrate or invertebrate comprising an avirulent derivative of a pathogenic microbe said derivative being substantially incapable of producing functional adenylate cyclase and cyclic AMP receptor protein.

This invention also provides a vaccine for the immunization of a vertebrate or invertebrate comprising an avirulent derivative of a microbe said derivative being incapable of producing functional adenylate cyclase and cyclic AMP receptor protein while being capable of expressing a recombinant gene derived from a pathogen of said vertebrate or invertebrate to produce an antigen capable of inducing an immune response in said vertebrate or invertebrate against said pathogen.

This invention also provides a method for stimulating the immune system in a vertebrate or invertebrate, comprising the step of:

administering to said vertebrate or invertebrate an avirulent vaccine for the immunization of a vertebrate or invertebrate comprising an avirulent derivative of a pathogenic microbe said derivative being incapable of producing functional adenylate cyclase and cyclic AMP receptor protein.

This invention also provides a method for stimulating the immune system in a vertebrate or invertebrate comprising the step of:

administering to said vertebrate or invertebrate an avirulent derivative of a microbe said derivative being incapable of producing functional adenylate cyclase and cyclic AMP receptor protein while being capable of expressing a recombinant gene derived from a pathogen of said vertebrate or invertebrate to produce an antigen capable of inducing an immune response in said vertebrate or invertebrate against said pathogen.

This invention also provides a carrier microbe for the synthesis of a vertebrate or invertebrate host protein comprising an avirulent derivative of a pathogenic microbe said derivative being incapable of producing functional adenylate cyclase and cyclic AMP receptor protein while being capable of expressing a recombinant gene derived from a vertebrate or invertebrate host to produce a product capable of suppressing, modulating, or augmenting an immune response in said vertebrate or invertebrate.

This invention also provides a method for regulating the immune response of a vertebrate or invertebrate comprising introducing into said vertebrate an avirulent derivative of a pathogenic microbe said derivative being incapable of producing functional adenylate cyclase and cyclic AMP receptor protein while being capable of expressing a recombinant gene derived from said vertebrate or invertebrate to produce a gene product capable of suppressing, modulating or augmenting the immune response of said vertebrate or invertebrate.

This invention also provides a method for desensitizing a vertebrate or invertebrate to an allergen comprising the step of administering to said vertebrate an avirulent derivative of a pathogenic microbe that expresses a recombinant gene derived from an organism producing an allergen active against said vertebrate or invertebrate to produce an antigen capable of desensitizing said vertebrate or invertebrate against said allergen of said vertebrate said avirulent derivative being incapable of producing functional adenylate cyclase and cyclic AMP receptor protein.

This invention also provides a method for producing an avirulent derivative of a pathogenic microbe said derivative being incapable of producing functional adenylate cyclase and cyclic AMP recepter protein comprising mutating the pathogenic microbe by means of transposon mutagenesis to form deletion mutations in each of the genes for adenylate cyclase and cyclic AMP receptor protein and isolating said derivatives. The same objective can also be achieved by using recombinant DNA techniques to generate deletions in the genes for adenylate cyclase and the cyclic AMP receptor proteins.

DETAILED DESCRIPTION OF THE FIGURES

Figure 3:
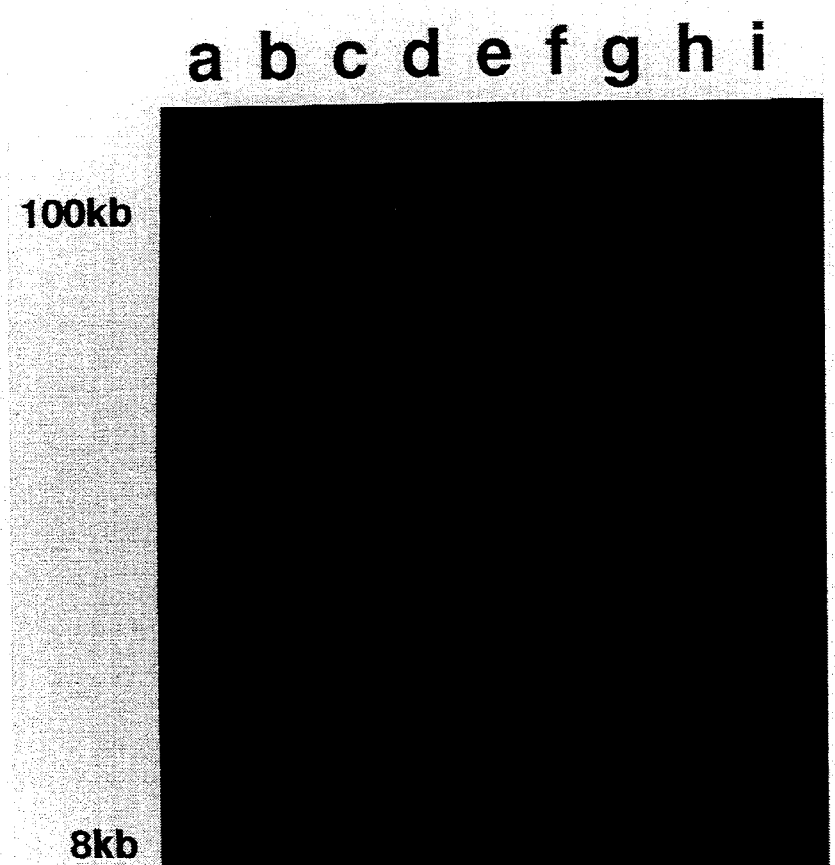

FIG. 3 illustrates the plasmid content of certain *S. typhimurium* strains. Plasmid DNA was extracted by the method of Birnboim (*Methods, Enzmol.* 100:243-255, 1983), resolved in a 0.5% (wt/vol) agarose gel, and stained with ethidium bromide. χ3344 and χ3337 lysates were extracted with phenol/chloroform/ether and not subjected to density gradient centrifugation. Strain (100 kb plasmid) in lanes: a, χ3000 (pStLT100); b, χ3344 (−); c, χ3347 (pStLT101); d, χ3306 (pStSR100); e, χ3337 (−); f, χ3338 (pStSR101); g, χ3339 (pStSL100, 90 kb, 8 kb); h, χ13340 (90 kb, 8 kb); i, χ3351 (pStSR101). Marker plasmids were Rldrd (100 kb) and dimeric pACYC184 (8 kb) (not shown).

Figure 4:
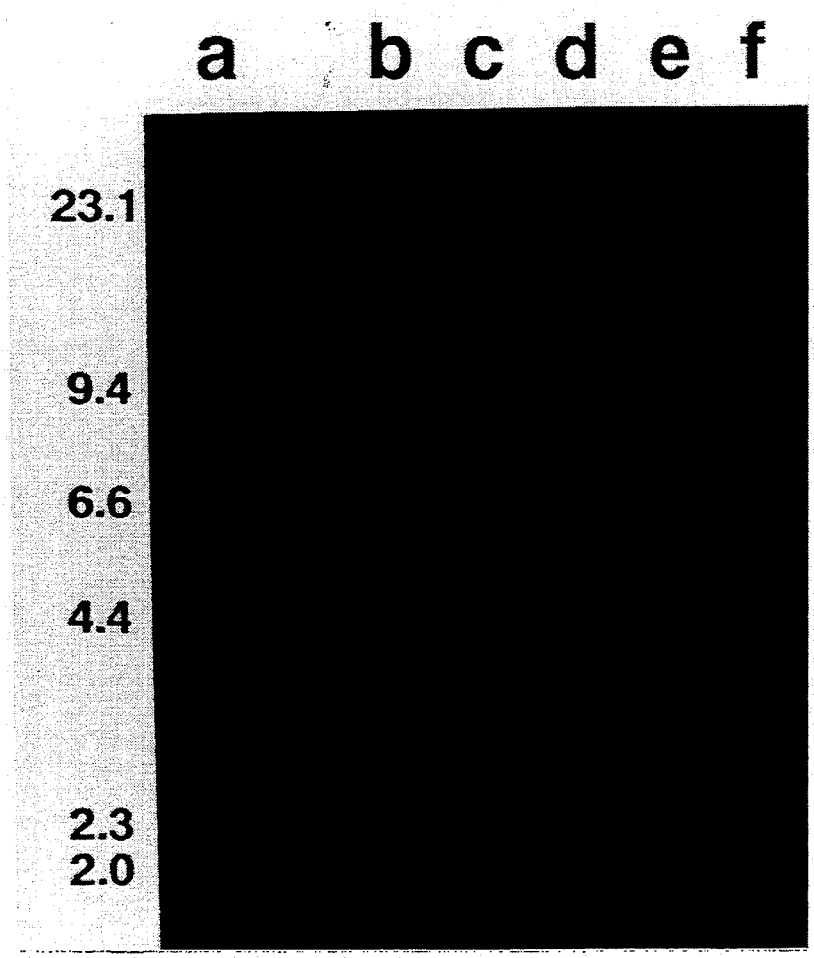

FIG. 4 illustrates the restriction enzyme digestion profiles of 100 kb plasmids. Plasmid DNA was digested with HindIII, resolved in a 0.6% (wt/vol) agarose gel, and stained with ethidium bromide. Lane a contains phage λDNA digested with HindIII. The following strains (and corresponding plasmid content) are shown in lanes: b,χ3000 (pStLT100); c, χ3306 (pStSR100); d, χ3338 (pStSR101); e, 3339(pStSL100, 90 kb, 8 kb); and f, χ3340 (90 kb, 8 kb).

Figure 5A:
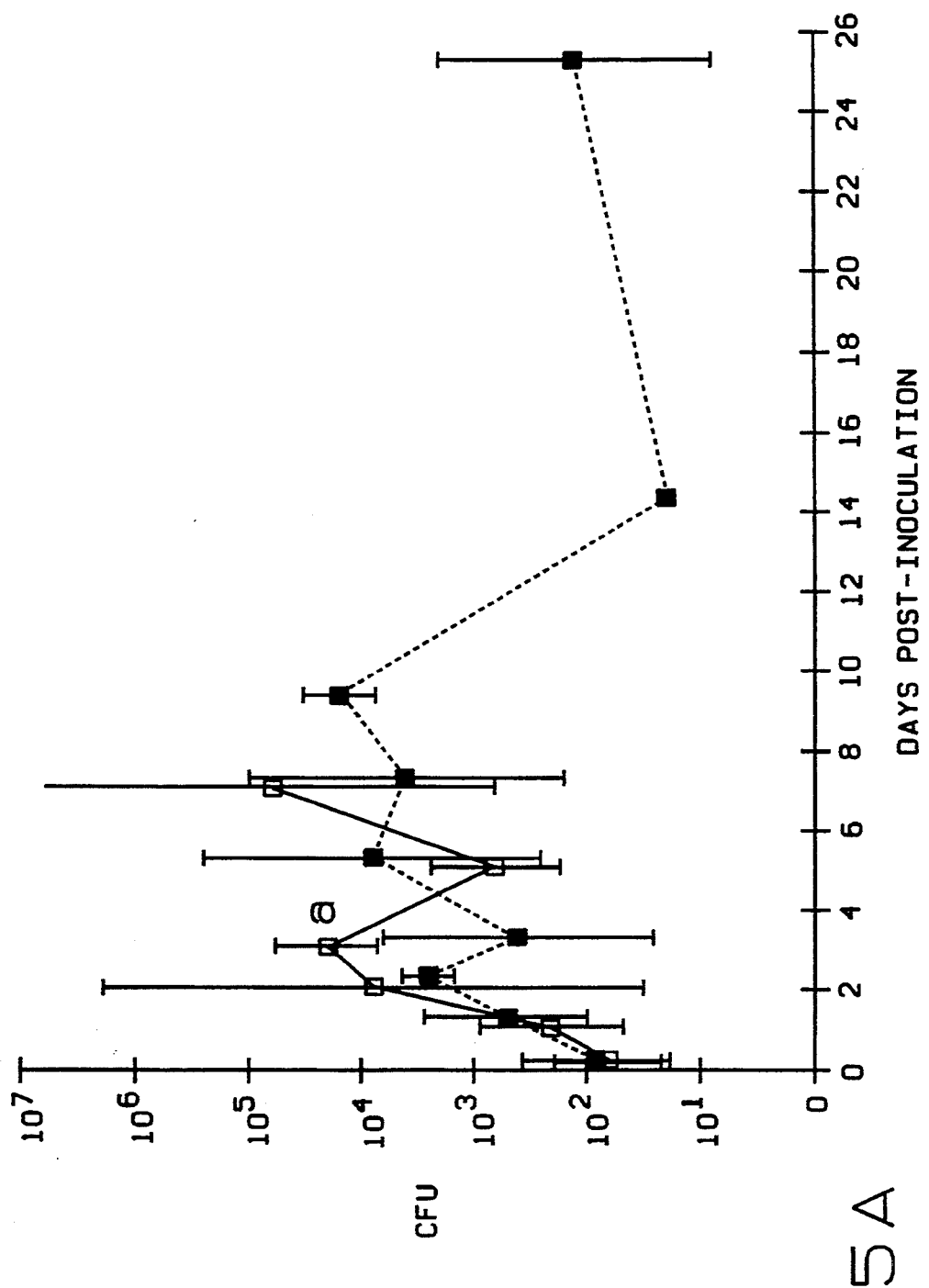
Figure 5B:
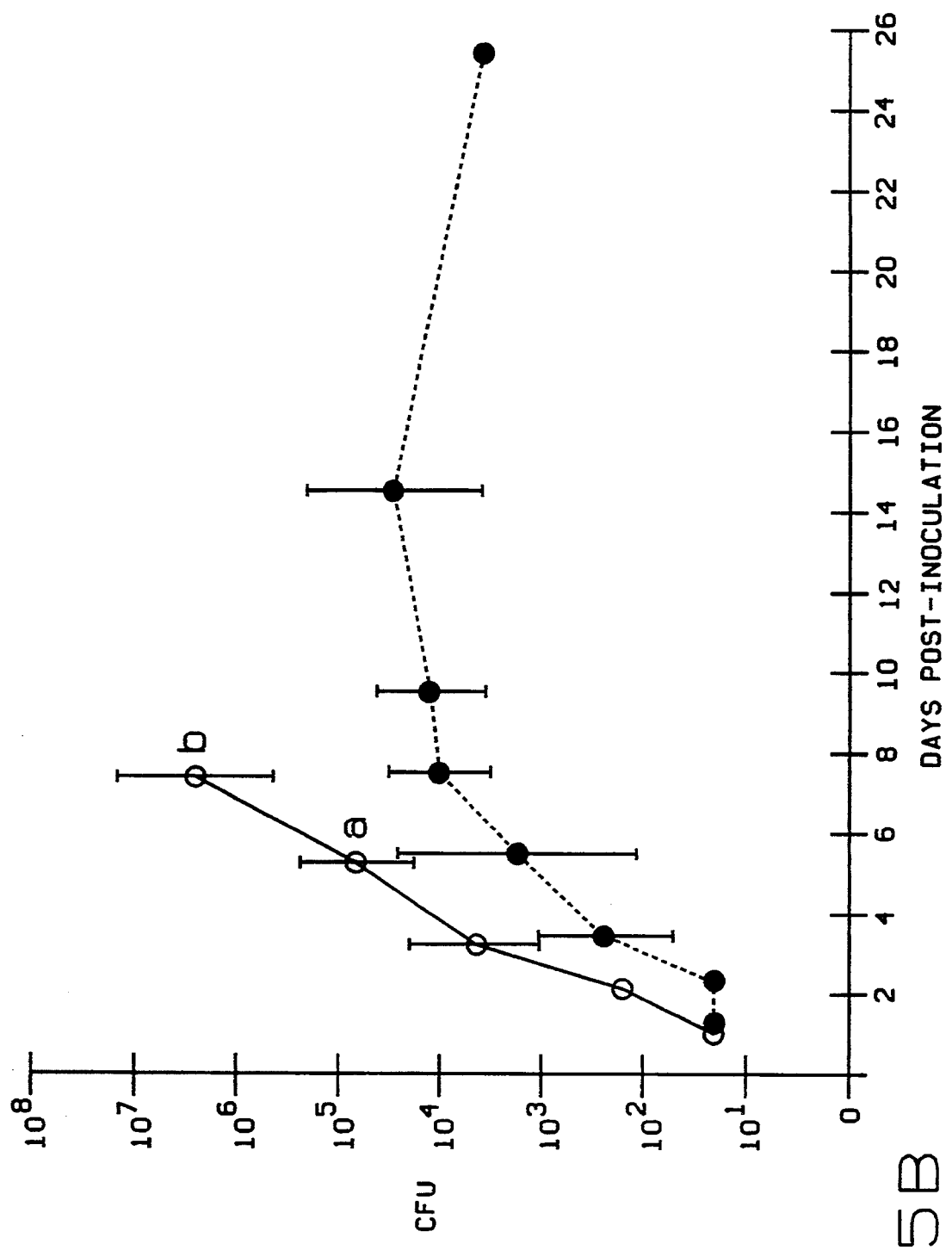

FIGS. 5A and 5B illustrate the total CFU in FIG. 5A Peyer's patches and FIG. 5B spleens after p.o. inoculation of mice with S. typhimurium SR-11. χ3306 (O,□), χ3337 (O,□). Geometric mean±SD, n=2 to 7 mice. P values in 1-tailed Student's t test for CFU χ3306 greater than χ3337: $^a$<0.0125, $^b$<0.0005.

Figure 6:
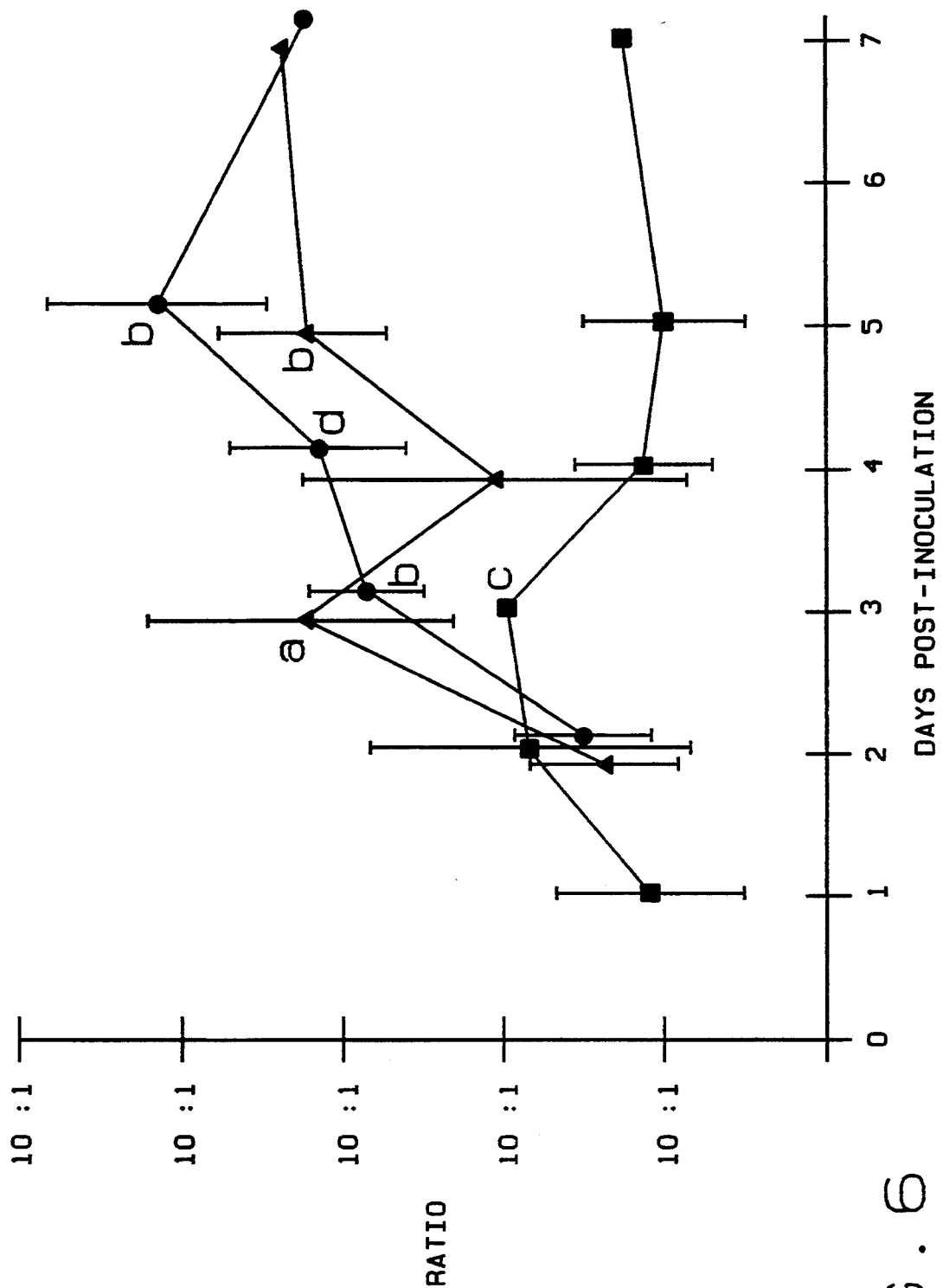

FIG. 6 illustrates the results of a mixed p.o. infection of mice with wild-type and 100 kb plasmid-cured SR-11. Geometric mean±SD of ratios of wild-type χ3456 to cured χ3337 recovered from Peyer's patches (O), mesenteric lymph nodes (Δ), and spleens (□). n=3 to 7 mice, n=1 for 7 days post-inoculation. P values in 1-tailed Student's t test for geometric mean of ratio greater than 1: $^a$<0.05, $^2$<0.0125, $^b$<0.0025, $^d$<0.0005.

Ratio of spleens was greater than ratio of Peyer's patches at 3 days (P<0.0125), 4 days (P<0.0005), and 5 days (P<0.0025) post-infection. Ratio of mesenteric lymph nodes was greater than ratio of Peyer's patches at 3 days (P<0.05) and 5 days (P<0.005) post-infection.

Figure 7:
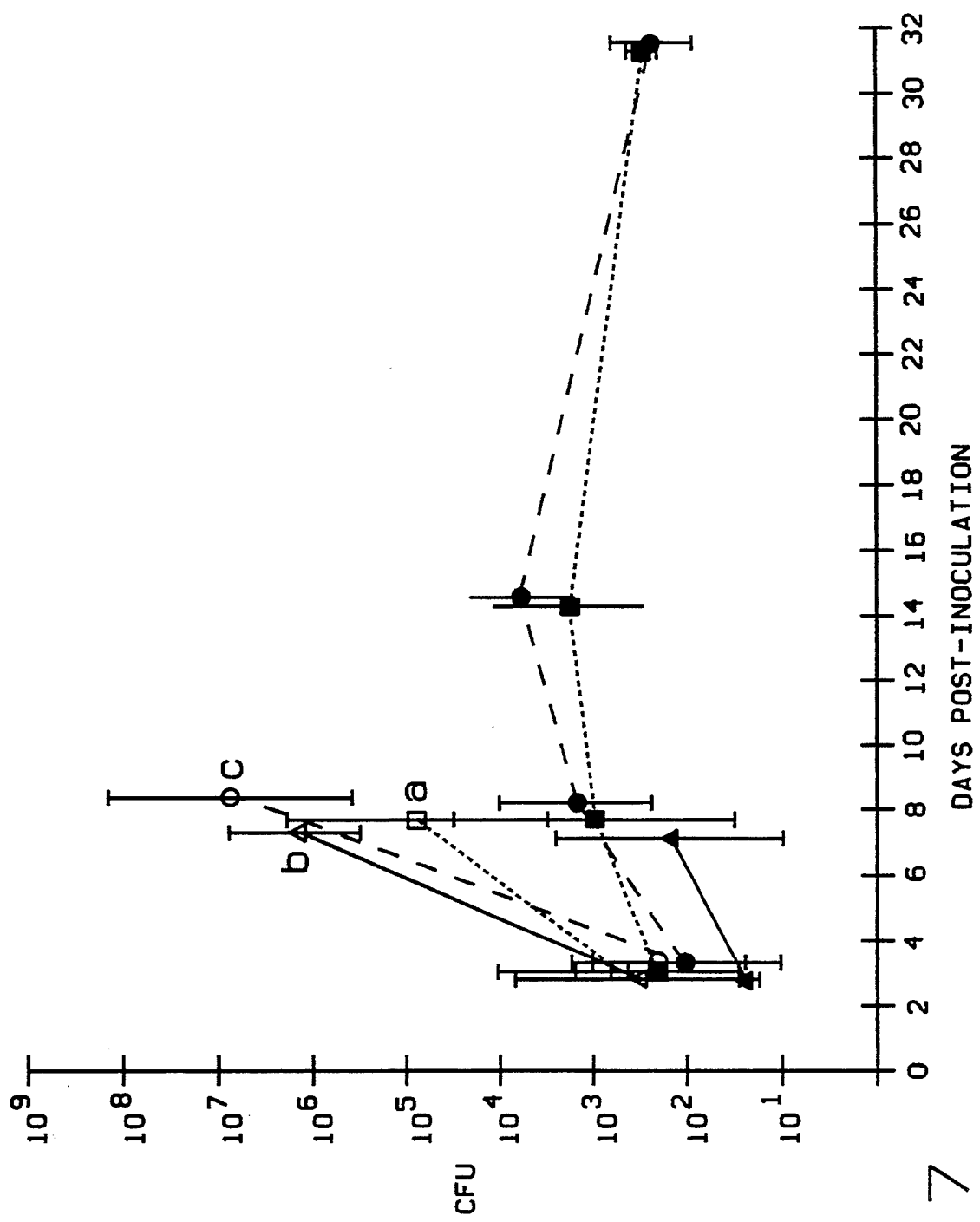

FIG. 7 illustrates the CFU in mouse tissues after p.o. inoculation of mice with SL1344. χ3339 (open symbols), χ3340 (filled symbols). Peyer's patches (□,■), mesenteric lymph nodes (Δ, ▲), spleens (O,●). Geometric mean±SD, n=2 to 7 mice. P values in a 1-tailed Student's t test for CFU χ3339 greater than χ3340: $^a$<0.025, $^b$<0.0125, $^c$<0.0005.

DETAILED DESCRIPTION OF THE INVENTION

This invention is predicated on the discovery that certain mutations can render a microbe avirulent without substantially affecting its immunogenicity. More specifically this invention relates to microbial vaccines in which the microbe carries the deletion (j) mutations ΔCya and Δqrp eliminating the ability to synthesize adenylate cyclase (ATP pyrophosphate lyase (cyclizing) EC 4.6.1.1) and the cyclic AMP receptor protein (CRP), respectively.

Cyclic-3'5'-AMP (cAMP) and the cyclic AMP receptor protein are necessary for the transcription of a large number of genes and operons concerned with the transport and breakdown of a large number of catabolites. Evidence has been provided that shows that systems used for transporting fuel/carbon sources are all under positive control by cAMP, as are several amino acid permeases. In addition to its very important role in catabolism, the cAMP concentration in cells also influences lysogenization by temperate phages, synthesis of fimbriae, synthesis of flagella and synthesis of at least one outer membrane protein. Although cAMP is present in mammalian cells, the concentrations present in macrophages and other cells in which Salmonella can invade and multiply are below the concentration of 0.1 to 1.0 mM cAMP necessary to allow Δcya mutants to exhibit a wild-type phenotype in vitro. Furthermore, the inclusion of the Δcrp mutation would essentially abolish any benefit that could accrue from uptake of cAMP in vivo by such Δcya mutants.

Once rendered avirulent by the introduction of the Δcya Δcrp mutations the microbes can serve as the immunogenic component of a vaccine to induce immunity against the microbe. Thus, the use of any microbe possessing the genes for adenylate cyclase and cAMP receptor proteins are contemplated by this invention, including but not limited to Salmonella, E. coli—S. typhimurium hybrids, Shigella, Erwinia, Yersinia, Pasteurella, Legionella or Brucella. Preferred microbes are members of the genus Salmonella such as S. typhimurium, S. typhi, S. paratyphi, S. gallinarum, S. enteritidis, S. choleraesuis, S. arizona, or S. dublin.

In another embodiment of the invention, the avirulent derivative of a pathogenic microbe also referred to herein as a carrier bacteria can be used to deliver selected antigens to the GALT, for example to the Peyer's patches of the ileum. Some genera of bacteria, such as Salmonella, are known to home to the Peyer's patches (Carter, P. B. and F. M. Collins, J. Exp. Med. 139:1189 (1974)). S. typhimurium-E. coli hybrids have also been shown to colonize Peyer's patches in mice (Hohmann, A. W., et al., Infect. and Immun. 22:763 (1978)). If these carrier bacteria contain and express a recombinant gene from a pathogenic organism, antibodies against the antigenic gene product produced from the pathogen will be induced. With the advent of recombinant DNA techniques, it now becomes possible to develop totally unique vaccines in which specific antigens are produced, not by the etiologic agent, but by another host strain of bacteria capable of expressing the gene for that antigen. It is also possible, when antigens might cross-react with an antigen of the mammalian host and thus potentiate the induction of autoimmunity, to use recombinant DNA techniques to alter the gene so that the affecting cross-reacting antigenic determinant is not produced. Thus, recombinant DNA techniques can be employed to develop vaccines that do not have any material capable of cross-reacting with vertebrate host antigens or capable to eliciting an autoimmune state.

It is apparent that the present invention has wide applicability to the development of effective vaccines against bacterial, fungal, parasite or viral disease agents where local immunity is important and might be a first line of defense. Some examples are vaccines for the control of pneumonic plague caused by Yersinia pestis, of gonorrhea caused by Neisseria gonorrhoeae, of syphilis caused by Treponema pallidum, and of veneral diseases as well as eye infections caused by Chlamydia trachomatis. Species of Streptococci from both group A and group B, such as those species that cause sore throat or heart diseases, Neisseria meningitidis, Mycoplasma pneumoniae, Hemophilus influenzae, Bordetella pertussis, Mycobacterium tuberculosis, Mycobacterium leprae, Bordetella avium, Escherichia coli, Streptococcus equi, Streptococcus pneumoniae, Brucella abortus, Pasteurella hemolytica, Vibrio cholera, Shigella species, and Legionella pneumophila are additional examples of bacteria within the scope of this invention from which genes could be obtained. Viral vaccines, such as those produced against influenza viruses, are also encompassed by this invention. Viral vaccines can also be produced against other viruses, either DNA or RNA viruses, for example from the classes Papovirus, Adenovirus, Herpesvirus, Poxvirus, Parvovirus, Reovirus, Picornavirus, Myxovirus, Paramyxovirus, or Retrovirus. Vaccines to protect against infection by pathogenic fungi, protozoa and parasites are also contemplated by this invention.

In a further embodiment when the immunogenic component of the vaccine is an allergen of the host such a vaccine may be used in an exposure regimen designed to specifically desensitize an allergic host.

In one of its embodiments, the invention can be described as a vaccine for the immunization of a vertebrate animal or invertebrate comprising a live avirulent derivative of a pathogenic microbe said derivative being incapable of producing functional adenylate cyclase and cAMP receptor protein while being capable of expressing a recombinant gene derived from an organism that is a pathogen of or that produces an allergen of said animal.

In yet another embodiment the avirulent microbes of this invention may be used as vectors for the synthesis of various host proteins. Because the avirulent microbes of this invention are able to traverse a variety of immunocompetent structures including GALT, mesenteric lymph nodes and spleen after introduction into the host, such microbes may be used to target a variety of immunoregulatory products. Accordingly, one or more genes encoding immunoregulatory proteins or peptides may be recombinantly introduced into the avirulent microbes such that when the microbes taking up residence in the appropriate immunocompetent tissue are capable of expressing the recombinant product to suppress, augment or modify the immune response in the host. Examples of immunoregulatory molecules include but are not limited to: colony stimulating factors (macrophage, granulocyte, or mixed), macrophage chemotoxin, macrophage inhibition factor, leukocyte inhibitory factors, lymphotoxins, blastogenic factor, interferon, and interleukins.

Still another embodiment of the subject invention is the use of the avirulent microbes contemplated herein to deliver and produce pharmacologically active products that might stimulate or suppress various physiological functions (i.e., growth rate, blood pressure, etc.).

Each of the terms in these embodiments of the invention is analyzed in the following discussion.

By vaccine is meant an agent used to stimulate the immune system of a living organism so that protection against future harm is provided. Immunization refers to the process of inducing a continuing high level of antibody and/or cellular immune response in which T-lymphocytes can either kill the pathogen and/or activate other cells (e.g. phagocytes) to do so in an organism, which is directed against a pathogen or antigen to which the organism has been previously exposed. Although the phrase "immune system" can encompass responses of unicellular organisms to the presence of foreign bodies, e.g., interferon production, in this application the phrase is restricted to the anatomical features and mechanisms by which a multi-cellular organism produces antibodies against an antigenic material which invades the cells of the organism or the extra-cellular fluid of the organism. The antibody so produced may belong to any of the immunological classes, such as immunoglobulins A, D, E, G, or M. Of particular interest are vaccines which stimulate production of immunoglobulin A (IgA) since this is the principle immunoglobulin produced by the secretory system of warm-blooded animals, although vaccines of the invention are not limited to those which stimulate IgA production. For example, vaccines of the nature described herein are likely to produce a broad range of other immune responses in addition to IgA formation, for example, cellular and humoral immunity. Immune response to antigens is well studied and widely reported. A survey of immunology is given in Barrett, James, T., Textbook of Immunology: Fourth Edition, C. V. Mosby Co., St. Louis, Mo. (1983), the entire of which is herein incorporated by reference.

A vertebrate is any member of the subphylum Vertebrata, a primary division of the phylum Chordata that includes the fishes, amphibians, reptiles, birds, and mammals, all of which are characterized by a segmented bony or cartilaginous spinal column. All vertebrates have a functional immune system and respond to antigens by producing antibodies. Thus all vertebrates are capable of responding to vaccines. Although vaccines are most commonly given to mammals, such as humans or dogs (rabies vaccine), vaccines for commercially raised vertebrates of other classes, such as the fishes and birds if of the nature described herein, are within the scope of the present invention.

An invertebrate is any member of the Animal Kingdom, excluding the vertebrates. Such animals constitute the Division Invertebrata and have no backbone or spinal column. This classification includes all animals except fishes, amphibians, reptiles, birds and mammals. Many invertebrates are capable of elliciting a primitive immune response to anitgenic stimulation and are susceptable to the same microorganisms which infect vertebrates adn which are disclosed herein in accordance with this invention. Exemplary of such invertebrates are shellfish and molluses and other related animals. Although the use of vaccines in the protection of invertebrate animals have hitherto before not been well documented, one skilled in the art will recognize the applicability of the subject invention to said invertebrates by use of their primitive immune systems. For example and in accordance with this invention, the susceptability of shellfish to infection by Salmonella will allow the introduction of avirulent strains of Salmonella species and thereby provide potential for the primitive immune system to respond. Therefore, it is within the scope of this invention, the use of an avirulent derivative of a pathogenic microbe, that is capable of infecting an invertebrate, to stimulate a response from an immune system present in said invertebrate against a pathogen.

In one embodiment of the invention is the use of an avirulent derivative of a pathogenic microbe that homes to the GALT or BALT as a carrier of the gene product which is used for stimulating antibody response against a pathogen or allergen. Avirulent does not mean that a microbe of that genus or species can not ever function as a pathogen, but that the particular microbe being used is avirulent with respect to the particular animal being treated. The microbe may belong to a genus or even a species that is normally pathogenic but must belong to a strain that is avirulent. By pathogenic is meant capable of causing disease or impairing normal physiological functioning. Avirulent strains are incapable of inducing a full suite of symptoms of the disease that is normally associated with its virulent pathogenic counterpart. Microbes as used herein include bacteria, protozoa, and unicellular fungi.

Techniques for transferring genetic material from a first organism to a second organism which normally does not exchange genetic material with the first organism, have recently become widely available as the result of rapidly expanding recombinant DNA technology. In this application, genetic material that has been transferred from one organism into a second in such a manner that reproduction of the second organism gives rise to descendents containing the same genetic material is referred to as a recombinant gene. The term gene is being used here in its broadest sense to represent any biological unit of heredity. It is not necessary that the recombinant gene be a complete gene as present in the parent organism, which was capable of producing or regulating the production of a macromolecule, for example, a functioning polypeptide. It is only necessary that the gene be capable of serving as the template used as a guide in the production of an antigenic product. The product may be one that was not found in that exact form in the parent organism. For example, a functional gene coding for a polypeptide antigen comprising 100 amino acid residues may be transferred in part into a carrier microbe so that a peptide comprising only 75, or even 10, amino acid residues is produced by the cellular mechanism of the host cell. However, if this gene product is an antigen that will cause formation of antibodies against a similar antigen present in the parent organism, the gene is considered to be within the scope of the term gene as defined in the present invention. Alternatively, if the amino acid sequence of a particular antigen or fragment thereof is known, it is possible to chemically synthesize the DNA fragment or analog thereof by means of automated gene synthesizers or the like and introduce said DNA sequence into the appropriate expression vector. At the other end of the spectrum is a long section of DNA coding for several gene products, one or all of which can be antigenic. Thus a gene as defined and claimed here is any unit of heredity capable of producing an antigen. The gene may be of chromosomal, plasmid, or viral origin.

In order for the gene to be effective in eliciting an immune response, the gene must be expressed. Expression of a gene means that the information inherent in the structure of the gene (the sequence of DNA bases) is transformed into a physical product in the form of a RNA molecule, polypeptide or other biological molecule by the biochemical mechanisms of the cell in which the gene is located. The biological molecule so produced is called the gene product. The term gene product as used here refers to any biological product or products produced as a result of the biochemical reactions that occur under the control of a gene. The gene product may be, for example, an RNA molecule, a peptide, or a product produced under the control of an enzyme or other molecule that is the initial product of the gene, i.e., a metabolic product. For example, a gene may first control the synthesis of an RNA molecule which is translated by the action of ribosomes into an enzyme which controls the formation of glycans in the environment external to the original cell in which the gene was found. The RNA molecule, the enzyme, and the glycan are all gene products as the term is used here. Any of these as well as many other types of gene products, such as glycoproteins and polysaccharides, will act as antigens if introduced into the immune system of an animal. Protein gene products, including glycoproteins and lipoproteins, are preferred gene products for use as antigens in vaccines.

In order for a vaccine to be effective in producing antibodies, the antigenic material must be released in such a way that the antibody-producing mechanism of the vaccinated animal can come into play. Therefore the microbe carrier of the gene product must be introduced into the animal. In order to stimulate a preferred response of the GALT or BALT cells as discussed previously, introduction of the microbe or gene product directly into the gut or bronchus is preferred, such as by oral administration, gastric intubation or in the form of aerosols, although other methods of administering the vaccine, such as intravenous, intramuscular, subcutaneous injection or intramammary or intrapenial or vaginal administration, are possible.

When the avirulent microbe is used, as a carrier microbe and once the carrier microbe is present in the animal, the antigen needs to become available to the animal's immune system. This may be accomplished when the carrier microbe dies so that the antigen molecules are released. Of course, the use of "leaky" avirulent mutants that release the contents of the periplasm without lysis is also possible. Alternatively, a gene may be selected that controls the production of an antigen that will be made available by the carrier cell to the outside environment prior to the death of the cell. In this way it is possible to use a viable microbe that will persist in the vaccinated animal, for example in its Peyer's patches, and continue to produce antigen, thereby continually inducing antibody formation. A preferred gene product under these circumstances is a product that is transferred through the cell membrane into the external environment or a product that becomes attached to or embedded in the external membrane so that all or part of the gene product is exposed to the environment. Typical of this latter type of gene product are antigens normally found on the surface of the organism against which protection is desired. If these antigens are transported to the cell surface in a normal manner, antibody formation against the antigens will be enhanced.

The use of pathogens to deliver antigens from other pathogens to the GALT or BALT would be inappropriate if it were not for the fact that such pathogens can be rendered avirulent while retaining ability to invade Peyer's patches or the BALT.

The organism from which the recombinant gene is derived may be any pathogen of the animal being vaccinated or may be an organism that produced an allergen or other antigen of the animal. Allergens are substances that cause allergic reaction, in this case in the animal which will be vaccinated against them. Many different materials may be allergens, such as animal dander and pollen, and the allergic reaction of individual animals will vary for any particular allergen. It is possible to induce tolerence to an allergen in an animal that normally shows an allergic response. The methods of inducing tolerence are well-known and generally comprise administering the allergen to the animal in increasing dosages. Further discussion of tolerence induction is given in the Barrett textbook previously cited. Lastly the host organism itself can serve as a source of genetic material when immunoregulatory genes or genes for other pharmacologically active substances are being expressed by the vectors.

Administration of a live vaccine of the type disclosed above to an animal may be by any known or standard technique. These include oral ingestion, gastric intubation, or broncho-nasal spraying. All of these methods allow the live vaccine to easily reach the GALT or BALT cells and induce antibody formation and are the preferred methods of administration. Other methods of administration, such as intravenous injection, that allow the carrier microbe to reach the animal's blood stream may be acceptable. Intravenous, intramuscular or intramammary injection are also acceptable with other embodiments of the invention, as is described later.

Since preferred methods of administration are oral ingestion, aerosol spray and gastric intubation, preferred carrier microbes are those that belong to species that home preferentially to any of the lymphoepithelial structures of the intestines or of the bronchii of the animal being vaccinated. These strains are preferred to be avirulent derivatives of enteropathogenic strains produced by genetic manipulation of enteropathogenic strains. Strains that home to Peyer's patches and thus directly stimulate production of IgA are most preferred. In animals these include specific strains of Salmonella, and Salmonella-E. coli hybrids that home to the Peyer's patches.

Recombinant DNA techniques are now sufficiently well known and widespread so as to be considered routine. In very general and broad terms, this method consists of transferring the genetic material, or more usually part of the genetic material, of one organism into a second organism so that the transferred genetic material becomes a permanent part of (recombines with) the genetic material of the organisms to which it is transferred. This usually consists of first obtaining a small piece of DNA from the parent organism either from a plasmid or a parent chromosome. A plasmid (also called an extrachromosomal element) is a hereditary unit that is physically separate from the chromosome of the cell. The DNA may be of any size and is often obtained by the action of a restriction endonuclease enzyme which acts to split DNA molecules at specific basepair sites. Following ligation to plasmid, phage or cosmid vectors to form recombinant molecules the recombinant molecules may be transferred into a host cell by various means such as transformation (uptake of naked DNA from the external environment, which can be artificially induced by the presence of various chemical agents, such as calcium ions). Other methods such as tranduction are also suitable, wherein the recombinant DNA is packaged within a phage such as transducing phage or cosmid vectors. Once the recombinant DNA is in the carrier cell, it may continue to exist as a separate piece (generally true of complete transmitted plasmids) or it may insert into the host cell chromosome and be reproduced with the chromosome during cell division.

Although transferring genetic material is relatively straightforward, predicting which transfers will result in expressed genes is not yet possible. This selection process, however, does not present any difficulty to the present invention. Since the host microbe must express the transferred gene and thereby produce an antigen, a "shotgun" approach works well. Antibodies are first produced against the desired antigen, for example, fragments of cell membranes from pathogenic microbes, by standard techniques. DNA from the organism that is the source of the antigen is cleaved into multiple fragments by endonucleases, and the fragments are inserted randomly into carrier microbes, preferably by means of cloning vectors. The microbes that express antigens from the pathogen can be easily identified by their reaction with antibody against pathogen antigens. Antigen-expressing microbes can be selected and cloned to give the desired recombinant organism. Shotgut cloning is well known and is described in detail in Maniatis, T., et al., *Molecular Cloning* Cold Spring Harbor Laboratories (1982), which is herein incorporated by reference. The techniques of gene transfer are not considered to be part of this invention, and any method capable of producing recombinant organisms comprising genes from an organism that are expressed in avirulent microbes will suffice.

In cases where the species normally exchange genetic information more classical methods of gene transfer may be employed such as conjugation, transformation or transduction.

Derivatives of avirulent microbes are also contemplated to be within the scope of this invention. By derivative is meant sexually or asexually derived progeny and mutants of the avirulent strains including single or multiple base substitutions, deletions, insertions or inversions which retain the inability to produce functinal adenylate cyclase and cAMP receptor protein with or without naturally occurring virulence plasmids. For example, strains such as $\chi 4062$ and $\chi 4064$ carry the gyrA mutation conferring nalidixic acid resistance which has been used herein as a convenient marker to follow strains following oral inoculation. However, drug resistance is not a desirable attribute for strains to be used as vaccines. Thus, the gyrA+ mutation can be easily removed by transducing the gyrA+ (conferring sensitivity to nalidixic acid) gene into strains by selecting for inheritance of a closely linked Tn10 and then removing Tn10 by selection for fusaric acid resistance.

The dosages required will vary with the antigencity of the gene product and need only be an amount sufficient to induce an immune response typical of existing vaccines. Routine experimentation will easily establish the required amount. Typical initial dosages of vaccine could be 0.001–1 mg antigen/kg body weight, with increasing amounts or multiple dosages used as needed to provide the desired level of protection.

The pharmaceutical carrier in which the vaccine is suspended or dissolved may be any solvent or solid or encapsulated in a material that is non-toxic to the inoculated animal and compatible with the carrier organism or antigenic gene product. Suitable pharmaceutical carriers include liquid carriers, such as normal saline and other non-toxic salts at or near physiological concentrations, and solid carriers, such as talc or sucrose and which can also be incorporated into feed for farm animals. Adjuvants may be added to enhance the antigenicity if desired. When used for administering via the bronchial tubes, the vaccine is preferably presented in the form of an aerosol.

Immunization with a pathogen derived gene product can also be used in conjunction with prior immunization with the avirulent derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the pathogen derived gene product to stimulate the lymphoid cells of the GALT or BALT. The enhanced response is known as a secondary, booster, or anamnestic response and results in prolonged immune protection of the host. Booster immunizations may be repeated numerous times with beneficial results.

The above disclosure generally describes the present invention. A more complete understanding can be obtained by reference to the following specific examples which are provided herein for purposes of illustration only and are not intended to be limiting unless otherwise specified.

Deposits of Strains Useful in Practicing the Invention

A deposit of biologically pure cultures of the following strains was made with the American Type Culture Collection (ATCC), 12301 Parklawn Drive, Rockville, Md. on Jul. 15, 1987 and the accession number indicated was assigned after successful viability testing, and the requisite fees were paid. Access to said cultures will be available during pendency of the patent application to one determined by the Commissioner to be entitled thereto under 37 C.F.R. S1.14 and 35 U.S.C. S122. All restriction on availablility of said cultures to the public will be irrevocably removed upon the granting of a patent based upon the application and said cultures will remain permanently available for a long term of at least five years after the date of deposit. Should the culture become nonviable or be inadvertently destroyed, it will be replaced with a viable culture(s) of the same taxonomic description.

| Strain | ATCC No. |
| --- | --- |
| χ4062 | 53647 |
| χ4064 | 53648 |

EXAMPLE 1

This Example demonstrates the construction of an avirulent microbe by the introduction of deletion mutations affecting cAMP synthesis and utilization.

Bacterial strains. The *Salmonella typhimurium* strains used are listed in Table 1. They were maintained as frozen cultures suspended in 1% Bacto-peptone containing 5% glycerol and fast-frozen in dry ice-ethanol for storage in duplicate at $-70°$ C. and also suspended in 1% Bacto-peptone containing 50% glycerol for storage at $-20°$ C. for routine use.

Media. Complex media for routine cultivation were L-broth (Lennox, *Virology* 1:190–206, (1965)) and Luria broth (Luria and Burrous, *J. Bacteriol.* 74:461–476 (1957)). Difco agar was added to Luria broth at 1.2% for base agar and 0.65% for soft agar. Penassay agar was used for routine enumeration of bacteria. Fermentation was evaluated by supplementing MacConkey base agar or Eosin methylene blue agar (Curtiss, *Genetics* 58:9–54 (1968)) with 1% final concentration of an appropriate carbohydrate.

Synthetic media were minimal liquid (ML) and minimal agar (MA) supplemented with nutrients at optimal levels as previously described (Curtiss, *J. Bact.* 89: 28–40, (1965)). Buffered saline with gelatine (BSG) (Curtiss, 1965 supra) was used routinely as a diluent.

Transduction. Bacteriophage P22 HT int was routinely used for transduction using standard methods (Davis et al., . . . . "A Man. for Genet Eng.-Adv Bact Genetics" Cold Spring Harbor Laboratory, Cold Spring Harbor, N.Y., (1979)). An overnight culture of the donor strain was diluted 1:20 into prewarmed Luria-broth, grown for 60 minutes with shaking at 37° C. and then infected with P22 HT int at a multiplicity of 0.01. The infection mixture was shaken overnight for approximately 15h, chloroform added and allowed to shake an additional 10 min at 37° C., and the suspension centrifuged (Sorvall RC5C, SS-34 rotor, 7,000 rpm, 10 min) to remove bacterial debris. The supernatant fluid containing the phage (ca. 10 /ml) was stored at 4° C. over chloroform. Tetracycline to a concentration of 12.5 μg/ml was used to select for transduction of Tn10-induced mutations.

Fusaric acid selection for deletion mutations. The media and methods described by Maloy and Nunn (*J. Bact.* 145:1110–1112, (1981)) were used. Strains with Tn10-induced mutations were grown overnight in L-broth containing 12.5 μg tetracycline/ml at 37° C. to approximately $5 \times 10^8$ cfu/ml. Cultures were then diluted 1:40 into prewarmed L-broth without tetracycline and aerated at 37° C. to a titer of about $2 \times 10^9$ cfu/ml. Suitable numbers of cells (i.e. $10^{7-108}$) diluted into BSG were plated on fusaric acid containing medium and incubated 48 h at 37° C. Fusaric acid-resistant isolates were purified on the same selective medium. Single isolates were picked, grown and tested for tetracycline sensitivity on Penassay agar with and without 12.5 μg tetracyline/ml.

Mice. Female BALB/c mice (Sasco, St. Louis, Mo.) were used for all infectivity and immunization experiments. Animals of 3 or 7 weeks of age were purchased and held for one week in a quarantined room prior to being used in experiments. Experimental mice were placed in Nalgene filter-covered cages with wire floors. Food and water were given ad libitum. The animal room was maintained at 22°–23° C. with a period of 12 hours illumination.

Animal infectivity. The virulence of *S. typhimurium* strains was determined following peroral or intraperitoneal inoculation. Bacteria for inoculation in mice were grown overnight as standing cultures at 37° C. in L-broth. These cultures were diluted 1:50 into prewarmed L-broth and aerated at 37° C. for approximately 4 h to an $OD_{600}$ of about 0.8–1.0. The cells were concentrated 50-fold by centrifugation in a GSA rotor at 7,000 rmp for 10 min at 4° C. in a Sorvall RC5C centrifuge followed by suspension in BSG. Suitable dilutions were plated on Penassay agar for titer determination and on MacConkey agar with 1% maltose to verify the Cya/Crp phenotype.

For all peroral inoculations, mice were deprived of food and water for 4 h prior to infection. They were than given 30 μl of 10% (w/v) sodium bicarbonate using a Pipetman P200 5 min prior to peroral feeding of 20 μl of *S. typhimurium* suspended in BSG using a Pipetman P20. Food and water were returned 30 min after oral inoculation. Morbidity and mortality of mice were observed over a 30-day period.

Intraperitoneal inoculation of unfasted mice was performed using a 26-gauge needle to deliver 300 μl of bacterial suspension diluted in BSG. Morbidity and mortality of mice were observed over a 30-day period.

Evaluation of protective immunity. In initial experiments, any mice that survived infection with any *S. typhimurium* mutant strain for 30 days were challenged on day 31 with $10^3$–$10^4$ times the $LD_{50}$ doses of the wild-type mouse-virulent *S. typhimurium* SR11 strain χ3306 by the peroral route. Susequently, groups of mice were perorally immunized with various doses of avirulent mutants and then challenged with various doses of virulent χ3306 cells at various times after the initial immunization. Morbity and mortality were observed throughout the experiment and for at least 30 days after challenge with χ3306 cells.

Enumeration of viable *S. typhimurium* cells in vivo. Colonization and persistence of wild-type and mutant *S. typhimurium* SR11 strains were determined following peroral inoculation of mice with approximately $1 \times 10^9$ cells by the methods described above. Titers of *S. typhimurium* cells were determined at 4, 24, 48, 72 and 96 hours and 7 days after peroral infection in the contents of the small intestine and colon and in homogenates of Peyer's patches (8–10), a 10 cm section of small intestinal wall located at the distal section of the ileum with Peyer's patches removed, and the colon wall. Titers of cells in homogenates of mesenteric lymph nodes and spleen were also determined. Mice were euthanized by $CO_2$ asphyxiation and the mesenteric lymph nodes, spleen, small intestine, and colon were immediately placed in chilled ML+15% sucrose minimal salts (MLS) which were held on ice. A petri dish containing 4.0 ml of chilled MLS was used to hold the small intestines while the Peyer's patches were removed with small surgical scissors. Peyer's patches were rinsed twice with 1 ml each of chilled BSG before placing into a glass screw-cap tube (15×100 mm) containing 1 ml chilled MLS and glass beads. The small intestine was then cut longitudinally and the contents and walls placed in a 50 ml disposable conical tube and chilled MLS was added to a 5.0 ml volume prior to vortexing for 1 min. A 10 cm section of small intestine was removed, rinsed twice in 5 ml BSG, and placed in a glass screw-cap tube (15×100 mm) containing 2.5 ml chilled MLS and glass beads. The contents of the small intestine were recovered from the chilled MLS used during longitudinal dissection and washing of the small intestine and added to the 50 ml disposable conical tube containing the small intestinal contents. A petri dish containing 4.0 ml of chilled MLS was used to hold the colon while it was cut longitudinally through the caecum. The contents of the colon and the colon wall were placed in a 50 ml final volume prior to vortexing for 1 min. The colon wall was then removed and rinsed twice in 5 ml BSG before placing into a glass screw-cap tube (15×100 mm) containing 2.5 ml chilled MLS and glass beads. The contents of the colon were collected from the chilled MLS used during longitudinal dissection and washing of the colon and added to the 50 ml disposable conical tube containing the colon contents. The mesenteric lymph nodes and connecting fatty tissue were placed in a glass screw-cap tube (15×100 mm) containing 1.0 ml chilled MLS and glass beads and vortexed. Spleens harvested at 96 h and 7 days are processed by placing directly into a Dounce pestle-type tissue homogenizer and grinding with 2.5 ml chilled MLS. Each tube with glass beads and tissue was vortexed for 4 to 5 min using a Super-mixer at high speed. Suspensions were diluted in BSG and plated on MacConkey agar containing 1% lactose and 40 μg nalidixic acid/ml. Total viable titers were determined by using the volumes of the suspensions, the dilutions, and the plate counts. MacConkey agars containing 1% of various carbohydrates were used to verify that the recovered organisms had the expected phenotype.

Construction of *S. typhimurium* SR11 strains with cya and crp mutations. The *S. typhimurium* SR11 strain χ3041 was used for peroral infection of BALB/c mice. A noticeably ill animal was sacrificed after 5 days and the subsequently verified fully mouse-virulent isolate χ3181 was recovered from a Peyer's patch. A gyrA mutation conferring resistance to nalidixic acid was introduced into χ3181 by P22 transduction to yield χ3306, the parent to all of the strains to be described herein (Table 1).

Since it has been shown that *S. typhimurium* isolates cured of the 100 kb virulence plasmid are fully able to attach to, invade and persist in Peyer's patches, but are defective in traversing to the mesenteric lymph nodes and spleen, cya and crp mutations were introduced into the plasmid-cured *S. typhimurium* SR11 strain χ3337 as well as into the plasmid-containing SR11 derivative χ3306. It should be emphasized that the reintroduction of the pStSR100 plasmid into χ3337 completely restores its virulence (See Example 3), thus insuring that no secondary mutations arose in χ3337 during the curing of the virulence plasmid.

TABLE 1

Bacterial strains

| Strain number | Parent strain/ plasmid | Relevant genotype | Derivation |
|---|---|---|---|
| χ3000 | LT2-Z/pStLT100 | prototroph | Charles Turnbough |
| χ3041 | SR-11/pStSR100 | virulent prototroph P22$^i$ | William Benjamin |
| χ3147 | LT2-Z/pStLT100 | gyrA1816 | spontaneous nalidixic acid-resistant mutant of χ3000 |
| χ3181 | SR-11/pStSR100 | prototroph | mouse-passaged χ3041 |
| χ3306 | SR-11/pStSR100 | gyrA1816 P22$^i$ | P22 HT int(χ3147) → χ3181 |
| χ3337 | SR-11 | gyrA1816 P22$^i$ | χ3306 cured of 100kb virulence plasmid |
| χ3456 | SR-11/PStSR101 | pStSR100::Tnminitet43 | P22 HT int(pStSR100::Tnminitet43 → χ3181 |
| PP1002 | LT2/pStLT100 | cya::Tn10 trpB223 | P. W. Postma; P22(PP991) → SB3507 (Postma et al., J. Bact 168: 1107–1111, |
| PP1037 | LT2/pStLT100 | crp773::Tn10 trpB223 | P. W. Postma; P22 (PP1011) → SB3507 (postma et al., |
| χ3395 | SR-11/pStSR100 | gyrA1816 cya::Tn10 | P22 HT int(PP1002) → χ3306 |
| χ3396 | SR-11/pStSR100 | gyrA1816 crp773::Tn10 | P22 HT int(PP1037) → χ3306 |
| χ4032 | SR-11/pStSR100 | gyrA1816 Δcya-1 | FA$^r$ Tc$^s$ derivative of χ3395 |
| χ4055 | SR-11/pStSR100 | gyrA1816 Δcya-1 crp773::Tn10 | P22 HT int(PP1037) → χ4032 |
| χ4058 | SR-11 | gyrA1816 cya::Tn10 | P22 HT int(PP1002) → χ3337 |
| χ4060 | SR-11 | gyrA1816 Δcya-3 | FA$^r$ Tc$^s$ derivative of χ4058 |
| χ4061 | SR-11 | gyrA1816 Δcya-3 crp773::Tn10 | P22 HT int(PP1037) → χ4060 |
| χ4062 | SR-11 | gyrA1816 Δcya-3 Δcrp-2 | FA$^r$ Tc$^s$ derivative of χ4061 |
| χ4064 | SR-11/pStSR100 | gyrA1816 Δcya-1 Δcrp-1 | FA$^r$ Tc$^s$ derivative of χ4055 |

Table 2 lists the phenotypic properties of all the mutant strains and their parents with regard to fermentation of sugars and growth on various carbon sources. The phenotypes are as expected based on published reports of the requirement for cyclic AMP and the cyclic AMP receptor protein for catabolic activities. (An exception is χ4060 which behaved like a Cya crp double mutant rather than a cya single mutant.) All cya/crp mutant strains lack fimbriae and flagella as expected based on previous results (Saier et al, *J. Bact.* 134(1):356–358, (1978); Yokota and Gots, *J. Bact.* 103:513–16 (1970); and Komeda et al., *Mol. Gen'l Genet.* 142:289–298, (1975)). It is also evident that the presence of the pStSR100 plasmid had no effect on these phenotypes.

At each step in the construction following selection of a fusaric acid-resistant tetracycline-sensitive derivative, an investigation as to whether tetracycline-resistant revertants/mutants could be recovered at frequencies higher than could be observed for the parental χ3306 strain was conducted. In all cases, such tetracycline-resistant revertants/mutants were not observed.

Virulence of mutant strains for mice. Preliminary information on virulence of mutant strains was obtained by infecting individual mice with either $10^5$ mutant cells intraperitoneally or $10^8$ mutant cells perorally and recording morbidity and mortality. Since χ3395 with the cya::Tn10 mutation and χ3396 with the crp::Tn10 mutation were apparently avirulent and since mice surviving infection with either become immune to challenge with wild-type χ3306 cells, further studies on the virulence of χ3395 and χ3396 were undertaken. Table 4 contains data which shows that mice survive infection with about 10 times the LD dose of either the cya::Tn10 mutant or the crp::Tn10 mutant. Studies were then initiated with strains in which the Tn10 and adjacent DNA sequences had been deleted. Table 5 presents data on morbidity and mortality of mice infected perorally with *S. typhimurium* wild-type, Δcya and Δcrp strains.

TABLE 2

Fermentation and growth properties of bacterial strains

| Strain number | Cya Crp pheno-type | | Fermentation phenotype on MacConkey agar containing:[a] | | | | | | | | Growth on Minimal agar containing: | | | | | | | | |
|---|---|---|---|---|---|---|---|---|---|---|---|---|---|---|---|---|---|---|---|
| | | | Frc | Gal | Glu | Glyc | Mal | Mtl | Mel | Srl | Cit | Gal | Glu | Glyc | Mal | Mtl | Mel | Srl | Suc |
| χ3306 | + | + | + | + | + | + | + | + | + | + | + | + | + | + | + | + | + | + | + |
| χ3395 | − | + | + | + | + | + | − | + | + | + | − | + | + | + | − | + | + | + | − |
| χ3396 | + | − | + | +/− | + | − | − | − | − | − | − | + | + | − | − | − | − | − | − |
| χ4032 | − | + | + | + | + | + | − | + | + | + | − | + | + | + | − | + | + | + | − |
| χ4060 | − | + | + | − | + | − | − | − | − | − | − | + | + | − | − | − | − | − | − |
| χ4062 | − | − | + | − | + | − | − | − | − | − | − | + | + | − | − | − | − | − | − |
| χ4064 | − | − | + | − | + | − | − | − | − | − | − | + | + | − | − | − | − | − | − |

[a]+ = positive for fermentation or growth; +/− = intermediate pink or haze-type growth; − = negative for fermentation or growth Colony diameters on MA containing 0.5% glucose as a function of incubation time and generation times in ML containing 0.5% glucose of several of the mutant strains and their parent are presented in Table 3. It is evident that the Δcya strains with or without the Δcrp mutation and independent of the presence or absence of the pStSR100 plasmid grow much more slowly than the parental χ3306 culture.

TABLE 3

Growth properties of bacterial strains.

| Strain number | Relevant genotype | Colony diameter (mm)[a] | | | Generation time[b] (min) |
|---|---|---|---|---|---|
| | | 40 h | 65 h | 87 h | |
| χ3306 | wild-type | 2.0 | 2.1 | 2.1 | 78 |
| χ3337 | wild-type | 2.0 | 2.1 | 2.1 | 82 |
| χ3395 | cya::Tn10 | 1.5 | 2.1 | 2.3 | 120 |
| χ3396 | crp773::Tn10 | 1.0 | 1.3 | 1.4 | 113 |
| χ4032 | Δcya-1 | 1.0 | 1.1 | 1.4 | 150 |
| χ4060 | Δcya-3 | 0.9 | 1.1 | 1.6 | 128 |
| χ4062 | Δcya-3 Δcrp-2 | 0.8 | 1.5 | 1.8 | 180 |
| χ4064 | Δcya-1 Δcrp-1 | 1.0 | 1.7 | 2.0 | 150 |

[a]Colonies distributed ~100 per plate on MA + 0.5% glucose
[b]Growth in ML + 0.5% glucose It is evident that irrespective of age of mice at the time of infection all mice survive infection with 1000–4000 wild-type $LD_{50}$ doses of any of the mutant strains. The information in Table 5 pertaining to avirulence of the pStSR100-cured derivative χ3337 are in accord with the more thorough studies presented in Example 3.

Table 6 presents additional data pertaining to infection with Δcya and Δcya Δcrp strains χ4060 and χ4062 (plasmid-cured) and χ4032 and χ4064 (plasmid-containing) which demonstrate that mice infected perorally with $1 \times 10^9$ bacteria grow essentially as well as do mice that remain uninfected.

Table 7 presents data for intraperitoneal challenge of the *S. typhimurium* mutants. Mice survived infection with $10^2$ to $10^3$ times the wild-type $LD_{50}$ dose for the various mutant strains. At higher doses, illness was observed which may be due in part to effects of endotoxin.

TABLE 4

Virulence of *S. typhimurium* SR-11 (cya::Tn10 and crp773::Tn10 in BALB/c female mice 30 days after peroral inoculation

| Strain number | Relevant genotype | Inoculating dose (cfu) | Age of mice[a] | Survival live/total | Mean day of death[b] | Health[c] |
|---|---|---|---|---|---|---|
| χ3306 | wild-type | $2.5 \times 10^5$ | 8 wk | 2/5 | 7 | scruffy |
| χ3395 | cya::Tn10 | $1.3 \times 10^9$ | 8 wk | 2/5 | 17 | scruffy |
| χ3396 | crp773::Tn10 | $2.4 \times 10^8$ | 8 wk | 5/5 | — | healthy |

[a]at time of immunization.
[b]of animals that died.
[c]healthy-no noticeable signs of disease; scruffy noticeably ill.

TABLE 5

Morbidity and mortality 30 days after peroral challenge of BALB/c mice with S. typhimurium SR-11 Δcya and/or Δcrp strains

| Strain number | Relevant genotype | pStSR100 | Inoculating dose (cfu) | Age of mice[a] | Survival live/total | Health[b] |
|---|---|---|---|---|---|---|
| χ3306 | wild-type | + | $2.5 \times 10^5$ | 8 wk | 3/6[c] | scruffy |
| χ3337 | wild-type | − | $5.0 \times 10^8$ | 8 wk | 6/6 | scruffy |
| χ4032 | Δcya-1 | + | $1.3 \times 10^9$ | 4 wk | 6/6 | healthy |
| χ4032 | Δcya-1 | + | $1.3 \times 10^9$ | 8 wk | 6/6 | healthy |
| χ4060 | Δcya-3 | − | $7.8 \times 10^8$ | 4 wk | 6/6 | healthy |
| χ4060 | Δcya-3 | − | $7.8 \times 10^8$ | 8 wk | 6/6 | healthy |
| χ4062 | Δcya-3 Δcrp-2 | − | $1.2 \times 10^9$ | 4 wk | 6/6 | healthy |
| χ4062 | Δcya-3 Δcrp-2 | − | $1.2 \times 10^9$ | 8 wk | 6/6 | healthy |
| χ4064 | Δcya-1 Δcrp-1 | + | $1.2 \times 10^9$ | 4 wk | 6/6 | healthy |
| χ4064 | Δcya-1 Δcrp-1 | + | $1.2 \times 10^9$ | 8 wk | 6/6 | healthy |

[a]at time of challenge.
[b]healthy-no noticeable signs of disease; scruffy-noticeably ill.
[c]Mean day of death = 7

TABLE 6

Evaluation of growth of 8 week-old BALB/c female mice 30 days after administering Δcya Δcrp S. typhimurium SR-11

| Strain number | Relevant genotype | pStSR100 | Inoculating dose (cfu) | Weight (in grams) at: | |
|---|---|---|---|---|---|
| | | | | Time of infection | 30 days post-infection |
| Control | | | uninfected | $19.2 \pm 0.3$ | $21.8 \pm 0.3$ |
| χ3395 | cya::Tn10 | + | $1.3 \times 10^9$ | $17.8 \pm 0.5$ | $18.9 \pm 3.0$ |
| χ3396 | crp773::Tn10 | + | $2.4 \times 10^8$ | $18.9 \pm 1.1$ | $20.5 \pm 1.3$ |
| χ4032 | Δcya-1 | | $8.6 \times 10^8$ | $19.8 \pm 0.5$ | $21.4 \pm 0.5$ |
| χ4060 | Δcya-3 | − | $8.8 \times 10^8$ | $19.4 \pm 0.6$ | $21.4 \pm 1.4$ |
| χ4062 | Δcya-3 Δcrp-2 | − | $6.8 \times 10^8$ | $20.1 \pm 0.2$ | $21.7 \pm 0.4$ |
| χ4064 | Δcya-1 Δcrp-1 | + | $1.0 \times 10^9$ | $19.9 \pm 0.4$ | $21.9 \pm 0.8$ |

TABLE 7

Morbidity and mortality 30 days after intraperitoneal challenge of 8 week-old BALB/c female mice with S. typhimurium SR-11 Δcya and/or Δcrp strains

| Strain number | Relevant genotype | pStSR100 | Challenge dose (cfu) | Survival live/total | Mean day of death[a] | Health[b] |
|---|---|---|---|---|---|---|
| χ3306 | wild-type | + | <50 | 3/6 | 7 | scruffy |
| χ3395 | cya::Tn10 | + | $1.0 \times 10^4$ | 0/5 | 12 | none |
| | | | $1.0 \times 10^5$ | 1/5 | 7 | scruffy |
| | | | $1.0 \times 10^6$ | 0/5 | 3 | none |
| χ3396 | crp773::Tn10 | + | $1.9 \times 10^4$ | 5/5 | — | healthy |
| | | | $1.9 \times 10^5$ | 4/5 | 18 | moderate |
| | | | $1.9 \times 10^6$ | 1/5 | 12 | scruffy |
| χ4062 | Δcya-3 Δcrp-2 | − | $1.0 \times 10^4$ | 5/5 | — | healthy |
| | | | $1.0 \times 10^5$ | 5/5 | — | healthy |
| | | | $1.0 \times 10^6$ | 0/5 | 10 | none |
| χ4064 | Δcya-1 Δcrp-1 | + | $1.6 \times 10^4$ | 5/5 | — | healthy |
| | | | $1.6 \times 10^5$ | 2/5 | 14 | scruffy |
| | | | $1.6 \times 10^6$ | 0/5 | 16 | none |

[a]of animals that died.
[b]healthy-no noticeable signs of disease; moderate-moderately ill; scruffy-noticeably ill.

Effectiveness of immunization with avirulent mutants. Table 8 presents data on the ability of the different S. typhimurium Δcya and Δcya Δcrp mutants to induce immunity to subsequent peroral challenge with $10^4$ times the LD$_{50}$ doses of fully virulent S. typhimurium SR11 χ3306 cells. Under these worse case challenges, many of the mice displayed moderate illness with decreased food consumption except mice immunized with χ4064 which remained healthy and ate and grew normally. Sacrifice of all animals (even those immunized with χ4064) 30 days post-challenge revealed spleenomeglia and ability to recover the χ3306 wild-type challenge strain but not the avirulent Δcya or Δcya Δcrp vaccine strains. In contrast, spleenomeglia and recovery of the challenge strain was not observed when mice immunized with approximately $1 \times 10^9$ χ4064 were challenged with only 100 to 1000 LD$_{50}$ doses of the fully virulent χ3306 parent strain.

Figure 1:
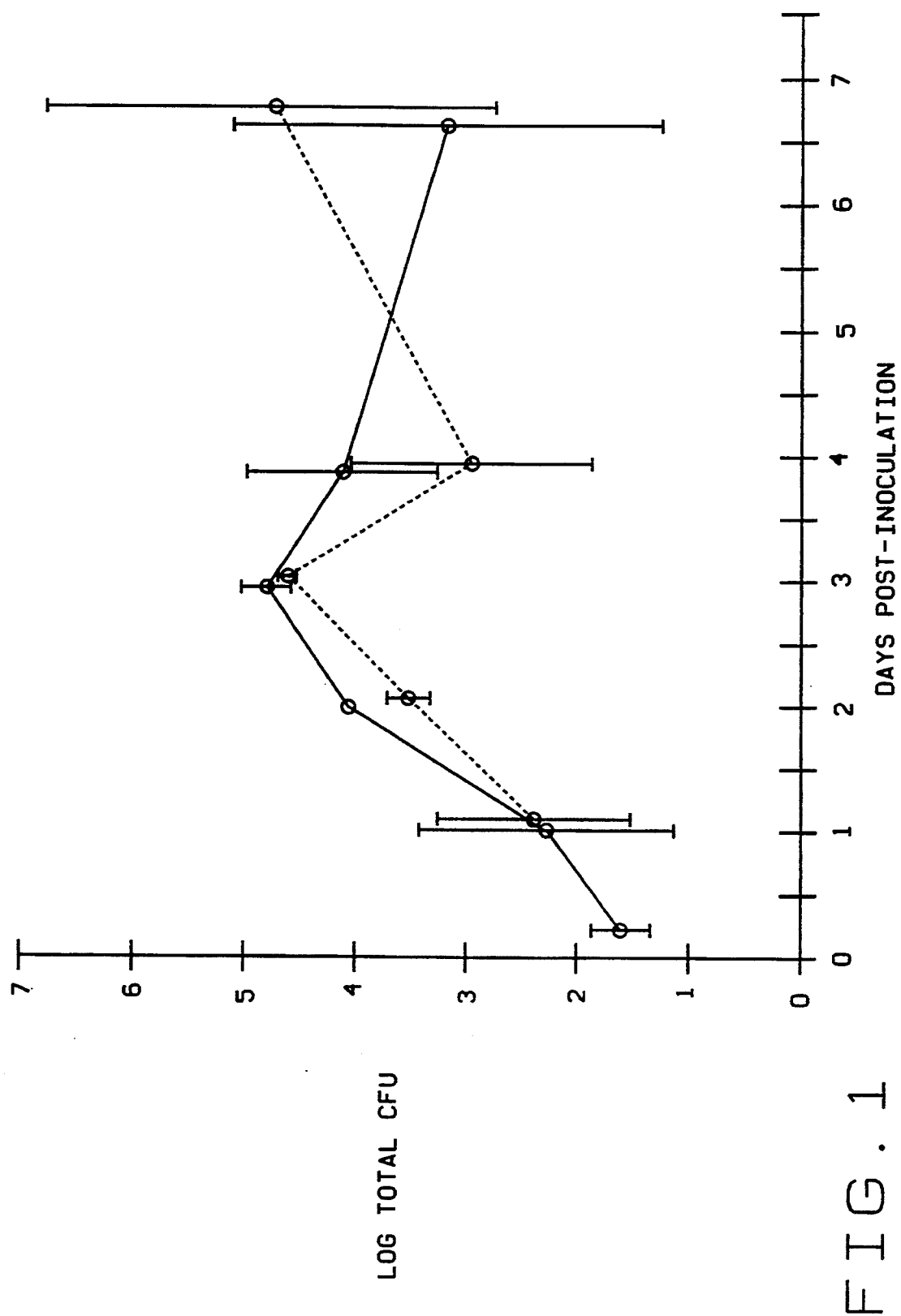
FIG. 1 illustrates the recovery of *S. typhimurium* Δcya Δcrp χ4064 (O) and wild-type χ3456 (O) from Peyer's patches (i.e., GALT) at specified time after peroral inoculation with $7.4 \times 10^8$ cfu of χ4064 and $4.0 \times 10^8$ cfu of χ3456. The vertical bars denote the standard deviations.
Figure 2:
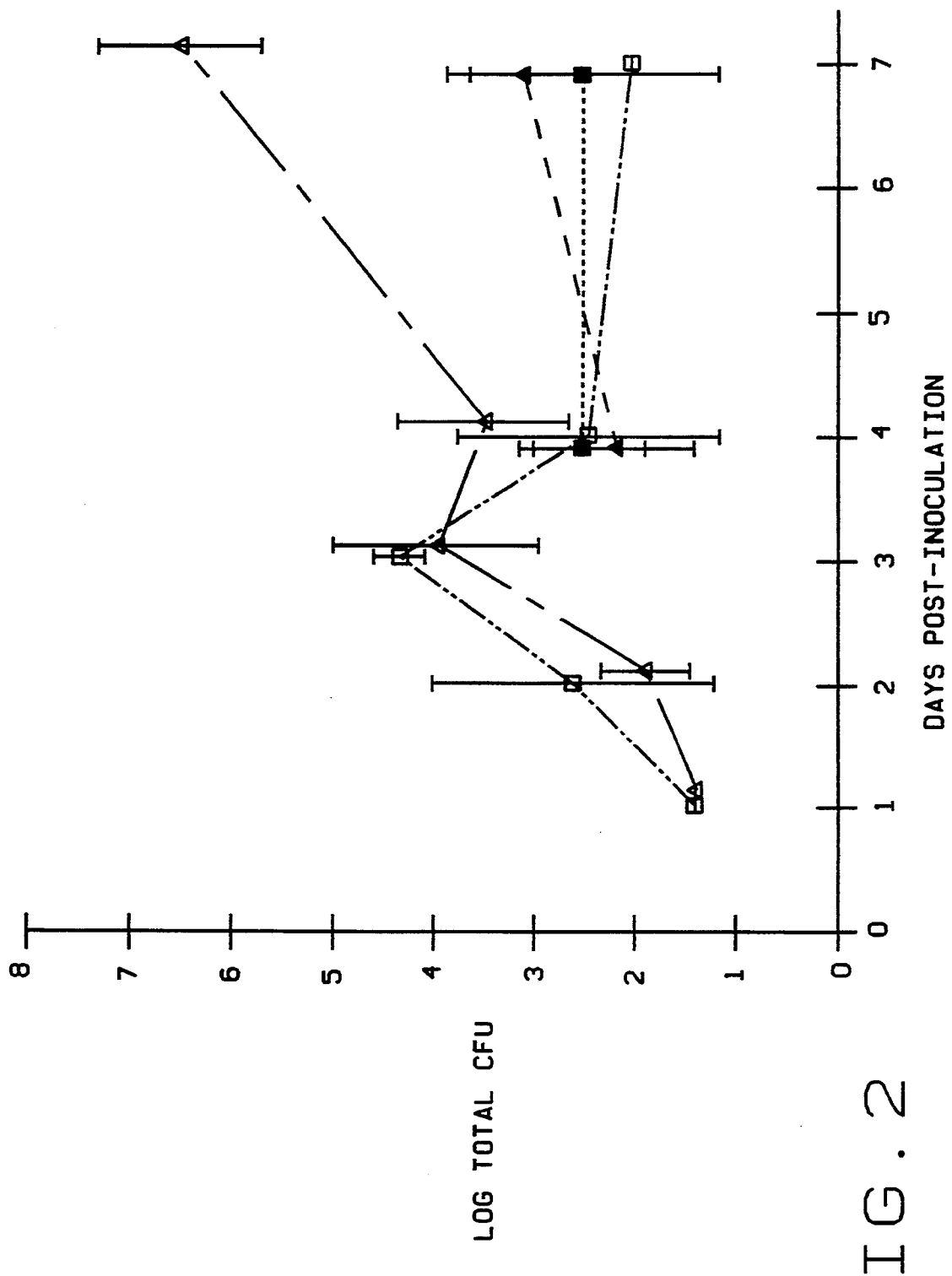
FIG. 2 illustrates the recovery of *S. typhimurium* Δcya Δcrp χ4064 (■▲) and wild-type χ3456 (□△) from mesenteric lymph nodes (■□) and spleen (▲△) at specified times after peroral inoculation with $7.4 \times 10^8$ cfu of χ4064 and $4.0 \times 10^8$ cfu of χ3456. The vertical bars denote the standard deviations.

Tissue trophism and persistence of avirulent mutants in vivo. FIGS. 1 and 2 present data on recovery of the Δcya Δcrp strain χ4064 in comparison to recovery of the nalidixic acid-sensitive wild-type strain χ3456 (Tn minitet-labelled; see Table 1) as a function of time following peroral inoculation. It is evident that the Δcya and Δcrp mutations do not significantly impair the ability of S. typhimurium to attach to, invade and persist in the Peyer's patches at least for a period of time sufficient to induce protective immunity (FIG. 1) but do impair ability to reach or survive in the spleen (FIG. 2).

TABLE 8

Effectiveness of immunization with avirulent *S. typhimurium* SR-11 Δcya Δcrp mutants in protecting against challenge with $2 \times 10^9$ cfu wild-type virulent *S. typhimurium* SR-11[a]

| Strain number | Relevant genotype | pStSR100 | Dose (cfu) of immunizing strain | Age of mice[b] | Survival live/total | Mean day of death[c] | Health[d] |
|---|---|---|---|---|---|---|---|
| χ4032 | Δcya-1 | + | $1.3 \times 10^9$ | 4 wk | 6/6 | — | moderate |
| χ4032 | Δcya-1 | + | $1.3 \times 10^9$ | 8 wk | 5/6 | 46 | moderate |
| χ4060 | Δcya-3 | — | $7.8 \times 10^8$ | 4 wk | 6/6 | — | moderate |
| χ4060 | Δcya-3 | — | $7.8 \times 10^8$ | 8 wk | 6/6 | — | moderate |
| χ4062 | Δcya-3 Δcrp-2 | — | $1.2 \times 10^9$ | 4 wk | 5/6 | 46 | moderate |
| χ4062 | Δcya-3 Δcrp-2 | — | $1.2 \times 10^9$ | 8 wk | 5/6 | 48 | moderate |
| χ4064 | Δcya-1 Δcrp-1 | + | $1.2 \times 10^9$ | 4 wk | 6/6 | — | healthy |
| χ4064 | Δcya-1 Δcrp-1 | + | $1.2 \times 10^9$ | 8 wk | 6/6 | — | healthy |

[a]Thirty days after immunization of 4 or 8 week-old mice with the strains indicated, mice were challenged with a per oral dose of $2.0 \times 10^9$ cfu of χ3306 wild-type virulent *S. typhimurium* SR-11.
[b]at time of immunization.
[c]following immunization of animal that died.
[d]healthy-no noticeable signs of disease or illness; moderate-moderately ill.

Genetic stability of avirulent mutants. Strains to be orally administered as live vaccines must have complete stability with regard to both their avirulence and their immunogenic attributes. Several of the candidate vaccine strains have therefore been grown in L-broth to late log phase with aeration, concentrated 50-fold and plated at various dilutions on a series of minimal agar media containing carbon sources that do not support the growth of the parent mutant (Table 2). A duplicate set of plates was exposed to ultraviolet light at an intensity that caused 70% cell death. Spontaneous revertants/mutants were observed at low but measurable frequencies (Table 9) in the Δcya strain χ4032 and at higher frequencies in the Δcya strain χ4060; many of these revertants were able to grow on most carbon sources and were therefore likely to be crp* (Scholte and Postma, *J. Bact.* 141:751-57 (1980); Garges and Adhya, *Cell* 41:745-51 (1985)) or csm (Melton et al., *Mol. Gen'l Genet.* 182:480-89 (1981)) mutations that permit CRP to activate transcription in the absence of cyclic AMP. Revertants/mutants from the Δcya Δcrp strains such as χ4064 were extremely rare (Table 9) and although able to grow on the carbon source (i.e., mannitol) on which they were selected, failed to grow on any of the other carbon sources the original strain failed to utilize (Table 2). These revertants/mutants undoubtedly have promoter mutations, causing transcription of the specific gene/operon to be independent of CRP. Ultraviolet light exposure did not enhance mutation/reversion frequencies.

Six revertants/mutants have been evaluated for virulence. Four mice were used to test each revertant. One received a peroral dose of $10^5$ cells, another a peroral dose of about $10^8$ cells, another an intraperitoneal dose of $10^2$ cells, and another an intraperitoneal dose of $10^5$ cells. In all instances, the four revertants from Δcya mutants and the two revertants of Δcya Δcyp strains retained the avirulence of their parent since all 32 mice remained healthy with no noticeable illness. It therefore appears that the avirulence of Δcya strains cannot be solely due to defective carbohydrate catabolism.

TABLE 9

Spontaneous reversion/mutation of Δcya Δcrp strains as revealed by plating 50-fold concentrated cultures on minimal agar with 0.5% final concentration of various carbohydrates

| Strain number | pStSR100 | Relevant genotype | Reversion frequency: | | | | | |
|---|---|---|---|---|---|---|---|---|
| | | | Mtl | Srl | Mal | Cit | Suc | Mel |
| χ4032 | + | Δcya-1 | $3.0 \times 10^{-5}$ | $3.0 \times 10^{-5}$ | 0 | 0 | 0 | 0 |
| χ4060 | — | Δcya-3 | TMTC[a] | TMTC | $2.0 \times 10^{-7}$ | $2.0 \times 10^{-7}$ | $2.0 \times 10^{-7}$ | TMTC |
| χ4062 | — | Δcya-3 Δcrp-2 | $2.7 \times 10^{-8}$ | 0 | 0 | 0 | 0 | 0 |
| χ4064 | + | Δcya-1 Δcrp-1 | $6.0 \times 10^{-8}$ | 0 | 0 | 0 | 0 | 0 |

[a]TMTC = Too many to count

The above result evidences the construction of a number of derivatives of the mouse virulent *S. typhimurium* SR11 strain χ3306 that lack the ability to synthesize adenylate cyclase and the cyclic AMP receptor protein and which do or do not possess the pStSR100 virulence plasmid. Although all strains are avirulent by the peroral route of inoculation and all induce a high level of protective immunity against subsequent challenge with virulent *S. typhimurium* wild-type cells, χ4062 and χ4064 which contain both Δcya and Δcrp mutations are preferred. The use of the double mutant with the deletion of the Crp gene precludes recovery of crp* mutations that permit transcription of genes and operons requiring activation by the CRP protein in the absence of any need for cyclic AMP. Similarly the absence of the crp gene also precludes the recovery of cms suppressor mutations that are closely linked to the crp gene, and which can also obviate the need for cyclic AMP. Even though the Δcya crp* or cms revertant strains tested remained avirulent, enough independent revertant isolates have not been tested for virulence to conclude that virulence could not be restored; therefore, the Δcrp mutation should preclude such restoration of virulence no matter how unlikely such changes might be. In addition, the Δcrp::Tn 10 mutation significantly reduces the virulence of *S. typhimurium* (Table 4) and therefore in the unlikely event that the Δcya mutation was lost by some type of gene transfer event, the Δcrp mutation would still render the strain avirulent.

The vaccine strain χ4064, which still possesses the pStSR100 plasmid, induces a higher level of immunity than does the plasmid-free strain χ4062 (Table 8). This is undoubtedly due to the increased ability of χ4064 (FIGS. 1 and 2) and plasmid-containing strains in general to achieve higher titers and persist longer than plasmid-free strains in mesenteric lymph nodes and spleen (see Example 3). On the other hand, immunization with χ4064 might be less well tolerated than immunization with χ4062 in young animals or in individuals that are malnourished or otherwise compromised. In this regard, if two immunizations were desirable, one could immunize first with χ4062 and then with χ4064.

A desired use of vaccine strains such as χ4062 and χ4064 is to serve as carriers to target colonization or virulence antigens expressed by genes from other pathogens to the gut-associated lymphoid tissue so as to induce a generalized secretory immune response and humoral and cellular immunity, if that should be desired. Therefore a variety of cloning vectors have been introduced into χ4062 and χ4064 and these plasmids exhibit a stability equal to or greater than in the wild-type parent strains. In fact, the slower rate of growth of χ4062 and χ4064 (Table 3) undoubtedly enhances the ability of plasmid replicons to keep up with chromosomal replication to insure that progeny cells contain plasmids. In addition, a variety of recombinant derivatives have been constructed and it was found that the colonizing antigen SpaA necessary for colonization of *S. mutans* and *S. sobrinus* to the salivary glycoprotein-coated tooth surface (Curtiss, *J. Dent. Res.* 65:1034–1045 (1986)) is expressed to a higher level in the Δcya crp mutants than in *S. typhimurium* strains with other mutations conferring avirulence.

EXAMPLE 2

This Example illustrates how the Δcya, Δcrp mutations may be introduced into other Salmonella species to render said species avirulent and thus useful as vaccine components.

Salmonella species useful for practicing this embodiment of the invention include *S. arizona* and *S. gallinarum* as avian Salmonella strains. *S. choleraesuis* as a porcine-specific Salmonella, *S. dublin* as a bovine-specific Salmonella, and a number of *S. typhimurium* derivatives that have been isolated from chickens, turkeys, veal calves, pigs and horses. These strains can be used to construct Δcya Δcrp mutants with and without virulence plasmids to evaluate protective immunity first in mice, and then in particular animal host species. These avirulent Salmonella derivatives can also be used to construct bivalent live vaccine strains for stimulation of protective immunity against the colonization and virulence proteins of other bacterial pathogens. Specifically, vaccines against *B. avium* and *E. coli*, two respiratory pathogens which are responsible for high morbidity and mortality in poultry and *Streptococcus equi*, which causes strangles in horses may be prepared.

Construction of Avirulent Salmonella strains

*S. typhimurium* LT-2 strains that possess cya::Tn10 or crp::Tn10 with the Δ[gal-uvrB]1005 mutation that renders a smooth or rough phenotype dependent upon the presence or absence of galactose, respectively, in the culture medium are used to generate the Δcya Δcrp genotype. Transduction with P22 HT int is used to introduce the cya::Tn10 and crp::Tn10 mutations into strains of *S. typhimurium* obtained from various hosts and into *S. typhi, S. paratyphi* and other Salmonella with similar 0 antigens. The rough-specific generalized transducing phage P1L4, is employed to introduce the Tn10-induced mutations into *S. arizona, S. gallinarum, S. dublin,* and *S. choleraesuis*. P1L4 transduction of the Salmonella species described above requires isolation of rough mutants. Selection for 2-deoxygalactose resistance results in galE mutants. The galE defect can ultimately be eliminated by transduction with P1L4 propagated on a rough mutant with the wild-type gal+ gene.

Stable deletion mutants are isolated by selection for fusaric acid-resistant derivatives of strains containing the cya::Tn10 and/or crp::Tn10 insertion mutations. Fusaric acid-resistant derivatives are tetracyline sensitive due to imprecise excision of the transposon and adjacent host chromosomal genes. When successive use of Tn10 is desired, it is necessary to verify that the fusaric acid-resistant isolates have completely lost Tn10, for example, by using a λ::Tn10 vector as a hybridization probe.

Salmonella strains cured of the virulence plasmid are constructed by using procedures and genetic tools developed for *S. typhimurium*. (See Examples 1 and 3). Tnmini-tet described by Way et al., (*Gene* 32:369–79 (1984)) is employed at this stage of construction. This transposon which lacks transposase and cannot spontaneously delete is inserted in the virulence-associated region of the 100 kb virulence plasmid that is probably homologous to the virulence plasmids of *S. dublin, S. gallinarum* and *S. choleraesuis* (Popoff et al., Ann. Microbiol. (Inst. Pasteur) 135A:389-398 (1984)). The transposon insertions are transduced into the homologous sequences of gale mutants of these other species. Tnmini-tet labeled virulence plasmids are cured by growing bacteria in novobiocin, a DNA gyrase inhibitor, at elevated temperatures of approximately 43° C. Curing of virulence plasmids can be verified by hybridization of cured derivatives with $^{32}$P-labeled native virulence plasmid.

All strains constructed are evaluated for stability of the genetic attributes and to determine that the phenotype displayed in *S. typhimurium* mutants is displayed in other Salmonella species. A last step to facilitate studies in animals is to introduce a drug resistance marker to assist in following the Salmonella strain during animal experimentation. Ordinarily resistance to either nalidixic acid or rifampicin is used since these resistances are not prevalent in the normal flora of mice, chickens, or turkeys.

Introducing some of the transposon-induced mutations into some of the Salmonella species by transduction may be impossible. Alternatively, conjugation may be beneficially employed wherein the transposon-induced mutation is cloned on a plasmid that can be mobilized from an Hfr with an integrated IncF or IncP plasmid into the Salmonella. Transformation provides yet a further alternative wherein the steps of selection for recombination of the sequence into the chromosome, elimination of the plasmid and verification of the precise genetic lesion are undertaken.

Evaluation of immunogenicity, colonization and persistence

The avirulent Salmonella strains constructed above may be evaluated in mice using peroral inoculation, gastric intubation, or intraperitoneal injection.

The procedure is initiated by growing Salmonella strains to log phase and concentrating them to nearly $10^{10}$ cells/ml in a buffered saline with gelatin. Animals to be inoculated perorally or by gastic intubation are deprived of food and water for 4 hours prior to inoculation. Sodium bicarbonate is administered to mice 5 minutes before the inoculation to neutralize stomach acidity. Food and water are given back to the mice 30 minutes after inoculation. Based on previous experiments with these mutant strains of *S. typhimnrium* in mice, ordinarily challenges with mice are with $10^3$ LD$_{50}$ doses. This might not be practical if the wild-type of the various Salmonella species do not give LD$_{50}$s as high as already observed for the mouse-virulent *S. typhimurium*. This becomes more of a problem for the peroral route of inoculation since administering more than $10^9$ organisms is difficult. Intraperitoneal inoculations may also be done at doses up to the level that would result in endotoxic shock (approximately $10^7$ cells). The weight and health condition of animals are monitored for one month.

Mice inoculated with the mutant Salmonella strain which survive for 30 days, are challenged with $10^3$ LD$_{50}$s of the virulent Salmonella parent strain by the peroral or intraperitoneal route. The health condition of the infected animals is followed daily with periodic evaluation for rate of growth. Prior to challenge, saliva samples are taken by pilocarpine stimulation, and each animal bled to collect serum. Quantitative titers of secretory IgA and IgG in saliva and of IgA and IgG in serum against Salmonella surface antigens are determined. The effect of secondary immunization on antibody titers and on persistence of immunity is also noted.

Vaccine strains which are avirulent, induce a high level of immunity and do not adversely affect weight gain, are used to determine the quantitative titers of the strain attached to the walls of the small bowel and colon and present in Peyer's patches, the small intestine and colon contents, the mesenteric lymph nodes, and in the spleen at 4, 24, 48, 72, and 96 hours and at weekly intervals thereafter if that should be necessary. This information is correlated with data on the immune response obtained.

Strains which are avirulent and immunogenic in mice, are then tested in the suitable animal species, e.g. *S. arizona*, *S. gallinarum* and avian *S. typhimurium* strains in chicks and turkey poults. Following evaluation of avirulence and immunogenicity in avian hosts, titers of virulent Salmonella in the crop, ceacum and Bursa of Fabricious are determined in addition to the tissues examined in mice.

Construction and testing of bivalent vaccine strains to immunize against Bordetella avium Vaccines against *B. avium* should express the surface structures involved in colonization and the antigenic but not toxic determinants of dermonecrotic toxin. Vaccines to surface proteins should produce immunity by blocking colonization of the trachea while antibodies to dermonecrotic toxin should neutralize its adverse effects. Although the *B. avium* surface structures involved in colonization are not known, the availability of gene libraries of *B. avium* in λgt11 expression vectors and transposon-induced *B. avium* mutants enable isolation and identification of genes encoding the surface proteins. By introducing the recombinant plasmids containing genes for surface proteins and/or dermonecrotic toxin determinants into an avirulent Salmonella, one can select a bivalent strain which induces protective immunity by preventing colonization (and thus identify genes involved in colonization) or by neutralizing toxin.

The genes for *B. avium* outer membrane proteins and/or dermonecrotic toxin are transferred to appropriate avirulent *S. arizona*, *S. gallinarum*, and/or *S. typhimurium* derivatives via transformation according to the method of Curtiss (Manual of Meth. in Bacteriol., ASM, Washington, D.C. (1981)), and expression of these proteins are examined using Western blot methods (Towbin et al, *Proc. Nat'l Acad. Sci.* (USA) 76:4350-54 (*1979*)). A 5 minute heat shock at 50° C. prior to transformation will be used to overcome any restriction barrier in Salmonella. Previous reports have indicated that Bordetella genes do not express efficiently in *E. coli* unless they are transcribed from an *E. coli* promoter. Such problems with expression of *B. avium* genes and transloctaion of the proteins to the outer membrane of Salmonella are eliminated by using a recombinant vector in which the gene will be fused to the *E. coli* lamb or ompA gene. In addition, the *B. avium* proteins would translocate to the outer membrane of Salmonella and enhance the probability of stimulating a stong immune response once the bivalent vaccine strain colonizes the Peyer's patches. Once *B. avium* genes are inserted into Salmonella, the recombinant clones are analyzed for expression of the genes by colony immunoblots using specific antibody and electron microscopy of immunolabeled Salmonella as disclosed by Chorbit et al, *EMBO J.* 5:3029-37 (1986).

One to three-day old poults are immunized perorally with the bivalent vaccine and serum and respiratory secretions are monitored to determine the type [IgY (IgG, 7S Ig), IgM, and IgA (IgB)] and quantity of the antibody response. Immunized and nonimmunized poults are compared for weight loss to monitor possible side-effects of the bivalent vaccine. In addition, turkey poults are challenged by intranasal inoculation with $10^9$ virulent *B. avium* or by exposure to infected birds. Challenged turkey poults are observed for disease, necropsied, and examined for tracheal tissue damage and changes in titers of the organism.

If a mucosal immune response against *B. avium* is inadequate to protect very young chickens and turkeys, breeding hens can be immunized with avirulent Salmonella expressing *B. avium* colonization and/or virulence antigens to permit egg transfer of maternal antibodies. Such treatment would augment immunity to *B. avium* while the young chicks or turkey poults are maturing. A protective peroral immunization employing the same recombinant carrier may also be administered during maturation.

Construction and testing of bivalent vaccine strains to immunize against avian *E. coli*

Recombinant clones that endow avirulent *E. coli* with increased virulence or the ability to colonize air sacs of chicks are introduced into avirulent strains of *S. gallinarum* and/or *S. typhimurium* by methods described above. The expression of virulence determinants on the Salmonella cell surface is determined by fluorescent antibody techniques, but it should be noted that *E. coli* cell surface determinants are likely to be expressed on the surface of Salmonella.

Chickens are immunized perorally with the bivalent vaccine strain and challenged by injecting virulent *E. coli* into the caudal air sac. If septicemia does not develop, birds are necropsied to determine if ability to colonize the air sac has been affected. Subsequently, a comprehensive study of the types, quantity, and duration of the antibody response in the respiratory secretions and serum as described above for turkey poults is conducted.

Techniques for vaccine administration and evaluation are the same as described previously for the *B. avium* vaccine.

Construction and testing of bivalent vaccine strains to confer immunity against Streptococcus equi Avirulent derivatives of S. typhimurium expressing the S. equi M protein have been constructed.

DNase I generated random fragments of the S. equi M protein gene are cloned into a λgt11 expression vector. The library is sequentially screened with antiserum against the M protein fragments that elicit protective immunity and antiserum against the M protein determinants present in the immune complexes of horses with purpura hemorrhagica. Cloned genes that express the protective, but not the purpuragenic, determinants are selected for fusion to either the 1amB or ompA gene. The immune response against avirulent Salmonella carrying those determinants is first investigated in mice and then in ponies or horses.

The availability of the described Salmonella strain expressing on its surface the relevant epitopes of the M protein of S. equi constitutes a very effective way of stimulating a mucosal nasopharyngeal protective immune response against strangles in the horse. The dissection of the purpuragenic determinants of the M protein contribute to the safety of the vaccine.

EXAMPLE 3

This Example illustrates the effect of virulence-plasmid deletion on the immunogenicity and virulence of several Salmonella strains.

Bacterial strains

The bacterial strains used in this Example are listed in Table 10 along with plasmid descriptions. Three lines of S. typhimurium strains were used: mouse-passaged, virulent strains SR-11 and SL1344 and the lesser virulent strain LT2. Escherichia coli HB101 and C600 were used in genetic manipulations.

Culture media and growth conditions. Unless otherwise stated, bacteria were grown in L broth or on L agar plates (Lennox, Virology 1:190–206 (1955)) supplemented with appropriate antibiotics at the following concentrations (ug/ml): ampicillin (Amp)—100–200, tetracycline (Tet)—12.5–25, chloramphenicol (Chl)—30, kanamycin (Kan)—50, streptomycin (Str)—50, and nalidixic acid (Nal)—50. For adherence, invasion, and macrophage infection some cultures were grown in Brain Heart Infusion broth (Difco, Detroit) because this medium increased bacterial adherence to the mammalian cells used. All cultures were grown overnight at 37° C. in static broths of the appropriate medium and were subcultured into shaking broths until late logarithmic phase of growth ($OD_{600}$ approximately 0.4–0.7).

Genetic exchange. Transformation was performed by using the method of Bagdasarian and Timmis (Curr. Top-Microbiol. Immunol. 96:47–67 (1981)). Phage P22 HT int-mediated transduction was performed as described by Schmeiger (Mol. Gen'l Genet. 119:75–88 (1972)). Conjugations were performed either by plate matings or filter matings (Willetts, Meth. in Microbiol. 17:33–58, (1984)).

TABLE 10

| | | Bacterial Strains | | |
|---|---|---|---|---|
| Strain | | 100 kb plasmid | Genotype | Description |
| S. typhimurium: | | | | |
| LT2-Z | χ3000 | pStLT100 | wild-type | from C. Turnbough (69) |
| | χ3147 | pStLT100 | gyrA1816 | spontaneous Nal$^r$ derivative of χ3000 |
| | χ3344 | — | | 100 kb plasmid-cured χ3000 |
| | χ3347 | pStLT101 | | pStLT101 (Tnmini-tet-labeled pStLT100 obtained by transposition from pNK561) transformed into χ3344, Tet$^r$ |
| | χ3477 | — | hsdL6, Δ[gal-uvrB]-1005, flaA66, rpsL120 xyl-404, lamB$^+$ (E. coli), Δ[zja::Tn101], hsdSA29 | used to obtain Rc chemotype LPS; S.A. Tinge and R. Curtiss (unpublished); Δ[galE-uvrB]-1005 obtained from B.A.D. Stocker in P22 HTint lysate from SL54000 |
| SR11 | χ3181 | pStSR100 | | SR-11 (57) isolated from Peyer's patch of an infected mouse; from Suzanne Michalek |
| | χ3306 | pStSR100 | gyrA1816 | gyrA1816 transduced into χ3181 from χ3147; mouse-passaged |
| | χ3337 | — | gyrA1816 | 100 kb plasmid-cured χ3306 |
| | χ3338 | pStSR101 | gyrA1816 | pStSR101 (Tnmini-tet-labeled pStSR100 obtained by transduction from χ3000[pStLT101]) transformed into χ3337, Tet$^r$ |
| | χ3456 | pStSR101 | | χ3181 with Tnmini-tet-labeled pStSR100 obtained by transduction from χ3000 (pStLT101]), Tet$^r$ |
| 1344 | χ3042 | pStSL100 | rpsL, hisG | from B.A.D. Stocker |
| | χ3339 | pStSL100 | rpsL, hisG | mouse-passaged χ3042 |
| | χ3340 | — | rpsL, hisG | 100 kb plasmid-cured χ3339 |
| | χ3351 | pStSR101 | rpsL, hisG | pStSR101 (Tnmini-tet-labeled pStSR100) transformed into χ3340, Tet$^r$ |
| E. coli: | | | | |
| K12 | | | F$^-$, thr-1, leuB6, tonA1, lacY1, λ$^-$, gyrA, thi-1 | spontaneous Nal$^r$ derivative of C600 |
| HB101 | | | F$^-$, ara-14, leuB6, proA2, lacY1, glnV44, galK2, λ$^-$, recA13, rpsL20, xyl-5, mtl-1, thi-1, hsdS20 ($r_B^-$,$m_B^-$) | |

DNA manipulations. Large scale and rapid minilysate plasmid extractions were performed using the method of Birnboim (Meth. Enzymol. 100:243–255 (1983)). Cesium chloride density gradient centrifugation, Southern blot hybridization, colony blot hybridization, and gel electrophoresis were performed using standard procedures. Nick-translation of DNA with [γ=P]ATP (Amersham, Arlington Heights, Ill.; specific activity=1445 Ci/mmol) was with the Bethesda Research Laboratories, Gaithersburg, Md. (BRL) kit according to manufacturer's instructions. Restriction enzyme digestions were with enzymes from BRL according to manufacturer's instructions.

Labeling the *S. typhimurium* 100 kb plasmid with Tnmini-tet. Strain χ3000 containing pStLT100 was transformed with pNK861, which possesses Tnmini-tet (Way et al., *Gene* 32:369-79 (1984)). Tnmini-tet is essentially the $Tet^R$ gene of Tn10 within inverted repeats. pNK861 was excluded from the library of $Amp^R$ $Tet^R$ χ3000 (pStLT100, pNK861) by mobilizing in the incompatable plasmid pNK259 from φ3000 (pNK259,F::Tn5) using F::Tn5. To select for Tnmini-tet insertions into the 100 kb plasmid, which is mobilizable by F, the χ3000::Tnmini-tet (pNK259, F::Tn5) library was mated with *E. coli* HB101 selected for $Tet^R$, $Kan^R$, and $Str^R$. Potential Tnmini-tet-labeled 100 kb plasmids in HB101 were mobilized back into *S. typhimurium* strain χ3147 by selecting for $Tet^R$ and $Nal^R$ Several $Nal^R$ $Tet^R$ $Kan^S$ isolates which did not possess F::Tn5 were picked.

Tnmini-tet insertions in the 100 kb plasmid were transduced into each of the 100 kb plasmid-containing, wild-type *S. typhimurium* strains by phage P22 HT int-mediated transduction. $Tet^R$ transductants were screened for increased size of the 100 kb plasmid and alteration in the restriction enzyme profile from that of the parental plasmid.

An alternative method for isolating pStLT100::Tnmini-tet insertions was to obtain plasmid DNA from χ3000 (pStLT100, pNK861) and to transform *E. coli* HB101 (pNK259), selecting for $Tet^R$ and $Chl^R$.

Curing *S. typhimurium* of the Tnmini-tet labeled 100 kb plasmid. *S. typhimurium* strains with Tnmini-tet insertions in the 100 kb plasmid were subjected to two curing regimens—growth at 43° C. or growth in broth containing novobiocin. Tnmini-tet-labeled strains were passaged daily with low inocula ($10^3$-$10^4$ colony-forming units [CFU]) for each of the curing regimens. When cultures had reached stationary phase ($OD_{600}$ approximately 0.9), a portion was diluted and plated on L agar containing fusaric acid. Fusaric acid-resistant colonies were screened for $Tet^S$, and plasmid contents of fusaric acid-resistant, $Tet^S$ colonies were examined by using minilysate analysis. Cured derivatives were further examined by Southern blot hybridization of minilysates and colony blot hybridization of bacterial cells with $^{32}$P-labeled pStSR100 to confirm curing and lack of a chromosomally integrated plasmid.

Mouse infections. Seven to 10 week-old female BALB/c mice (Harlan Sprague/Dawley [Indianapolis] and Sasco St. Louis]) were used for all animal infections. Older mice were used to obtain peritoneal macrophages. Normal mouse serum was obtained from male mice of various ages.

For p.o. inoculation, mice were food- and water-starved for 6 hours, then fed 50 μl of 10%(wt/vol) sodium bicarbonate, followed by 20 μl of bacteria suspended in buffered saline containing 0.1% (wt/vol) gelatin (BSG). Per oral inoculation was with a micropipet tip placed directly behind the incisors to avoid damage to the oral mucosa. Mice were fed food and water 30 minutes post-inoculation.

For i.p. inoculation and lateral tail vein intravenous (i.v.) inoculation, unfasted mice were injected with 0.1-0.2 ml of bacteria suspended in BSG.

Organs and tissues of infected mice were examined for presence of Salmonella as follows. Mice were killed by $CO_2$ asphyxiation. Spleens were aseptically removed and homogenized in 2.5 ml BSG in either an OMNI-mixer equipped with a microcup (Dupont, Wilmington, Del.) or a glass tissue homogenizer. Peyer's patches were removed from small intestines and washed twice by vortexing in 2 ml BSG. Rinsed Peyer's patches were homogenized in 2.5 ml BSG in either an OMNI-mixer or by vortexing in glass tubes containing glass beads. Mesenteric lymph nodes were homogenized in 2.5 ml BSG in glass tissue homogenizers. Dilutions of tissue and organ homogenates were plated on L agar plates containing appropriate antibiotics.

Statistical methods. For comparison of CFU in tissues of mice infected with either wild-type or cured *S. typhimurium*, geometric means were determined and compared in a 1-tailed Student's t test for wild-type CFU being greater than cured CFU. For analysis of mixed infections, geometric means of ratios of wild-type to plasmid-cured CFU from individual mice were compared in a 1-tailed Student's t test for mean of $\log_{10}$ of ratios greater than 0 (ratios greater than 1). Mouse $LD_{50}$ values were determined by the method of Reed and Muench (*Amer. J. Hyg.* 27:493-497 (1938)). Bacterial CFU in tissue culture and macrophage infections were compared by Student's t test of mean CFU/well in a 2-tailed test.

Presence of 100 kb plasmids in *S. typhimurium* strains. All three strains of *S. typhimurium* studied possessed 100 kb plasmids (FIG. 3). In addition, χ3339 possessed two other plasmids of 90 kb and 8 kb. The following three-part nomenclature system for 100 kb plasmids of the *S. typhimurium* strains was used in this study. To identify the serotype as *S. typhimurium*, the designation "St" was included. The strain designation ("LT" for LT2, "SR" for SR-11, and "SL" for SL1344) follows. A numerical designation finally identifies the plasmid as being wild-type (100) or a derivative (101 for a particular Tnmini-tet insertion, etc.). The wild-type plasmid of strain SR-11 therefore is pStSR100. Purified plasmid preparations were analyzed by restriction enzyme digestion, and identical profiles were obtained for the 100 kb plasmids from all three strains with HindIII (FIG. 4) and EcoRI (data not shown). Restriction enzyme digestion of the 100 kb plasmid-cured SL1344, χ3340, (FIG. 4, lane f) showed loss of the bands that correspond to the bands from pStLT100 (FIG. 4, lane b) and pStSR100 (FIG. 4, lane c), which were present in χ3339 (lane e). Therefore, the 100 kb plasmids of each of the three *S. typhimurium* strains examined in these studies were very similar, if not identical.

Strain construction. The transposon Tnmini-tet described by Way et al. (supra) was used to label 100 kb plasmids with a Tet-resistance marker. Tnmini-tet, a Tn10 derivative, does not possess the IS10R transposase gene within the inverted repeats hence the transposase gene is lost upon transposition from the donor plasmid, pNK861, and cannot subsequently mediate transposition or deletion of Tnmini-tet. Therefore, Tnmini-tet insertions are much more stable than those of the parent, Tn10.

A Tnmini-tet insertion into the 100 kb plasmid of strain 3000, resulting in pStLT101, allowed selection of derivatives cured of the 100 kb plasmid with a frequency of $10^{-6}$ to $10^{-7}$ cell$^{-1}$ generation$^{-1}$ following growth in novobiocin or growth at 43° C., yielding χ3344. This same Tnmini-tet insertion was then transduced into χ3339 and χ3306 and was used to cure these strains of their 100 kb plasmids, yielding χ3340 and χ3337, respectively. χ3340 retained the 90 kb and 8 kb plasmids (FIG. 3, lane h). Curing of 100 kb plasmids was confirmed by gel-electrophoresis of plasmid DNA from cleared lysates (FIG. 3) and hybridization of minilysates in Southern blots and lysed bacteria in colony blots with $^{32}$P-labeled pStSR100 (data not shown). Lack of hybridization in colony blots of the cured derivatives indicated that no chromosomally integrated plasmid was present. No plasmid-cured derivatives that possessed integrated plasmids were observed.

Tnmini-tet-labeled plasmids of χ3000, pStLT101, and χ3306, pStSR101, were reintroduced into cured derivatives by transformation, yielding χ3347 and χ3338, respectively. pStSR101 was transformed into χ3340, yielding χ3351 (Table 3, FIG. 3, lane i).

Mouse-virulence. The p.o. LD$_{50}$s in BALB/c mice of each of the wild-type, cured, and retransformed derivatives were determined (Table 11). The p.o. LD$_{50}$s of the mouse-passaged χ3306 and χ3339 were $3\times10$ CFU respectively, and the p.o. LD$_{50}$ of χ3000 was $>10^8$ CFU. The p.o. LD$_{50}$s of the respective cured derivatives were $>10^8$ CFU. Mice infected with χ3337 and χ3340 became sick, and occasional deaths were observed. The LD$_{50}$s of the 100 kb plasmid-retransformed derivatives were returned to those of the parental wild-type strains. This confirmed that the genetic lesion of cured derivatives was, in fact, loss of the 100 kb plasmid.

TABLE 11

Mouse LD$_{50}$ values$^a$ (CFU) for wild-type and 100 kb plasmid-cured S. typhimurium

| Strain | 100 kb plasmid | p.o. | i.p. |
|---|---|---|---|
| SR-11: | | | |
| χ3306 | + | $3 \times 10^5$ | <50 |
| χ3337 | − | $>10^8$ | <50$^b$ |
| χ3338 | + | $10^5$ | <50 |
| SL1344: | | | |
| χ3339 | + | $6 \times 10^4$ | <50 |
| χ3340 | − | $>6 \times 10^8$ | 400 |
| χ3351 | + | $<5 \times 10^4$ | <50 |
| LT2-Z: | | | |
| χ3000 | + | $>10^8$ | $2 \times 10^3$ |
| χ3344 | − | NT$^c$ | $2 \times 10^3$ |
| χ3347 | + | $>10^9$ | NT |

$^a$Determined by the method of Reed and Meunsch (supra)
$^b$Mean time to death for χ3337 (12.3 days) greater than that of χ3306 (7.0 days) (p < 0.001 Student's t test).
$^c$NT-not tested I.p. LD$_{50}$s of wild-type and cured derivatives were not as different as were p.o. LD$_{50}$s (Table 11). The i.p. LD$_{50}$s of χ3306 and χ3339 were <50 CFU, with 100% mortality achieved with each of these inocula. The cured derivative of χ3306, χ3337 also killed most mice injected with less than 50 CFU. However, the mean time to death was greater for 3337 (12.3 days) relative to χ3306 (7.0 days) (p<0.001, 1 tailed student's test). In contrast, the i.p. LD$_{50}$ of 100 kb plasmid-cured SL1344, 3340, was raised to 400 CFU from <50 CFU. Reintroduction of the Tmini-tet-labeled 100 kb plasmid into χ3340 restored the wild-type i.p. LD$_{50}$. The i.p. LD$_{50}$s for wild-type and cured LT2 strains were each approximately 2000 CFU.

Effects of plasmid exchange between strains SR-11 and LT2. Strain LT2 was much less virulent that strain SR-11 by the p.o. route (Table 11). To determine if the 100 kb plasmids of these two strains had a role in this difference in virulence, the Tnmini-tet derivatives of each of the 100 kb plasmids were transformed into the heterologous cured strains. Mice infected p.o. with $10^9$ CFU of strain SR-11 possessing either pStLT101 or pStSR101 died by 7 days post-inoculation, while strain LT2 was avirulent (p.o. inoculum $10^9$ CFU) with either plasmid. Therefore, the avirulence of strain LT2 was not due to defects in its 100 kb plasmid. This result, in addition to that obtained by introducing the SR-11 plasmid, pStSR101, into strain SL1344 yielding virulent χ3351 (Table 11), demonstrated that the 100 kb plasmids of these three strains were functionally equivalent.

Pathogenesis after p.o. inoculation. The more distinct differences in virulence between wild-type and cured derivatives by the p.o. route versus the i.p. route raised the possibility that the 100 kb plasmid was involved in virulence in the gut instead of during later stages of invasive disease. To examine this possibility, mice were infected p.o., with either wild-type SR-11, χ3306, or 100 kb plasmid-cured SR-11, χ3337, and Peyer's patches and spleens were examined for S. typhimurium at various times post-infection. The composite results of three experiments are presented in FIG. 5. At 3 hours post-infection, very few S. typhimurium were detected in Peyer's patches (<100CFU). This was not the result of inefficient passage of inocula from the oral cavity to the intestines as essentially 100% of inocula were recovered from the gut, primarily large intestinal contents, within 2 hours post-inoculation. Furthermore, CFU in the small intestinal contents were equal between wild-type and cured SR-11 up to 3 days post-inoculation. At 1 and 2 days post-inoculation, CFU in Peyer's patches gradually increased to $10^3$ to $10^4$ CFU, and CFU in spleens remained low. At 3 days post-inoculation, Peyer's patches and spleens possessed significantly more wild-type χ3306 than cured χ3337. The difference in CFU in Peyer's patches was not consistently observed in different experiments and, as the data for other time points indicate, was temporary. However, CFU in spleens remained significantly different with χ3306 outnumbering χ3337 in increasing amounts until mice infected with χ3306 died by 8 days post-inoculation. χ3337 in spleens reached levels on the order of $10^4$ CFU and remained detectable in spleens as long as 25 days post-inoculation. Thus, the primary difference in pathogenesis after p.o. inoculation between wild-type and virulence plasmid-cured S. typhimurium SR-11 was in the numbers of S. typhimurium reaching and/or multiplying in spleens.

To more precisely compare the relative virulences of wild-type and plasmid-cured SR-11, mixed infection experiments with Tet$^R$, wild-type SR-11, χ3456, and Nal$^R$, plasmid-cured SR-11, χ3337, were done. Ratios of wild-type CFU to plasmid-cured CFU were determined for each mouse. In addition, ratios of CFU were determined for mesenteric lymph nodes, which are intermediate in the invasive process from Peyer's patches to spleens. Large ranges in CFU and ratios between individual mice were observed, necessitating analysis of geometric means of ratios. Composite results of three experiments are presented in FIG. 6. As observed for the experiments with mice infected with either wild-type or plasmid-cured S. typhimurium (FIG. 5), no significant differences in CFU in Peyer's patches or spleens were detectable in mice with mixed infections until 3 days post-inoculation when wild-type to cured ratios in Peyer's patches, mesenteric lymph nodes, and spleens were 11:1, 200:1, and 79:1, respectively. At 4 days post-inoculation, only the ratio for spleens was significantly greater than 1.0 (ratio=160:1), while Peyer's patches and mesenteric lymph nodes had ratios of 1.5:1 and 13:1, respectively. Again, as observed in mice with separate infections, CFU in Peyer's patches were approximately equal for wild-type and cured SR-11 after the transient differences noted at 3 days post-inoculation. At 5 days post-inoculation, mesenteric lymph nodes and spleens possessed ratios of 200:1 and 1600:1, respectively; the Peyer's patch ratio was 1.1:1. At 7 days post-inoculation, a single mouse survived with Peyer's patch, mesenteric lymph node, and spleen ratios of 2.1:1, 290:1, and 210:1, respectively. The greatest differences in CFU in the various organs were in spleen and mesenteric lymph nodes relative to Peyer's patches. At 3, 4, and 5 days post-inoculation, spleen ratios were significantly greater than Peyer's patch ratios, and at 3 and 5 days post-inoculation mesenteric lymph mode ratios were significantly greater than Peyer's patch ratios (FIG. 6).

The pathogenesis of wild-type SL1344, $\chi$3339, and 100 kb plasmid-cured SL1344, $\chi$3340, was investigated in mice infected p.o. Results of two experiments are presented in FIG. 7. At 3 days post-inoculation, no significant differences in CFU in Peyer's patches, mesenteric lymph nodes, or spleens were observed between wild-type and cured SL1344. At 7 to 8 days post-inoculation, significantly greater numbers of wild-type $\chi$3339 than cured $\chi$3340 were detected in all three organs. Greater differences were observed in mesenteric lymph nodes and spleens than in Peyer's patches. Furthermore, in one of the experiments, the difference in CFU in Peyer's patches was not significant. Thus, infection of mesenteric lymph nodes and spleens represented the major consistent difference in pathogenicities between wild-type and 100 kb plasmid-cured SL1344. By 14 days post-inoculation, all mice infected with wild-type $\chi$3339 had died, while mice infected with cured $\chi$3340 had infection of Peyer's patches and spleens of $2 \times 10^3$ CFU and $6.3 \times 10^3$ CFU, respectively. At 31 days post-inoculation, Peyer's patches and spleens of mice infected with 3340 possessed 400 CFU and 320 CFU, respectively. Thus, 100 kb plasmid-cured SL1344 survived in Peyer's patches and spleens for extended periods of time after p.o. inoculation.

Infection of spleens after i.v. inoculation. The results described above indicated that the 100 kb plasmid was primarily involved in invasiveness from Peyer's patches to mesenteric lymph nodes and spleens after p.o. inoculation, instead of being involved in infection of Peyer's patches or earlier events. To examine growth of S. typhimurium in spleens, mice were inoculated i.v. with mixtures of wild-type SR-11, $\chi$3456, and plasmid cured SR-11, $\chi$3337, and spleens were monitored for CFU (Table 12). When mice were inoculated i.v. with $10^5$ CFU of $\chi$3456 and $\chi$3337, the strains were equally cleared to spleens 1 hour post-inoculation. Thus, presence of the 100 kb plasmid did not affect clearance from the blood. Other mice were inoculated i.v. with $1 \times 10^3$ to $4 \times 10^3$ CFU of mixtures of $\chi$3456 and $\chi$3337. No significant differences in CFU in spleens were detected at 4 days post-inoculation (Table 12). However, at 6 to 7 days post-inoculation, ratios of wild-type to cured S. typhimurium recovered from spleens were 11.5:1. At this time, mean levels in spleens of $\chi$3456 and $\chi$3337 were $2.7 \times 10^6$ and $2.3 \times 10^5$ CFU, respectively. Thus, plasmid-cured SR-11 survived and replicated in spleens for extended periods of time after i.v. inoculation. The wild-type to cured ratio for SR-11 in spleens of 11.5:1 at 1 week post-i.v. inoculation contrasted sharply with the ratios of 1600:1 and 210:1 obtained 5 and 7 days after p.o. inoculation. The lower ratio obtained with mixed i.v. inoculation was not due to synergy between $\chi$3456 and $\chi$3337 because at 6 days post-inoculation, mice infected with $2 \times 10^3$ CFU of $\chi$3337 alone or $\chi$3337 mixed with equal amounts of $\chi$3456 attained mean spleen levels of $2.3 \times 10^5$ CFU for $\chi$3337 (Table 12).

TABLE 12

| Infection of spleens after i.v. inoculation of mice[a] | | | |
|---|---|---|---|
| | Time post-inoculation | | |
| | 1 h[b] | 4 d[c] | 6–7 d[c] |
| CFU $\chi$3456[d] | $1.9 \times 10^5$ | $4.6 \times 10^4$ | $2.7 \times 10^6$ |
| CFU $\chi$3337[d] | $1.4 \times 10^5$ | $2.5 \times 10^4$ | $2.3 \times 10^{5e}$ |
| Ratio ($\chi$3456:$\chi$3337)[f] | 1.3:1 | 1.8:1 | 11.5:1 (P < 0.0025) |
| Ratio ± SD[g] | 0.11 ± 0.25 | 0.26 ± 0.38 | 1.06 ± 0.39 |

[a]Mice were inoculated i.v. with equal mixtures of wild-type $\chi$3456 and 100 kb plasmid-cured $\chi$3337. n = 3 to 5 mice.
[b]Inoculum = $5 \times 10^5$ CFU each of $\chi$3456 and X3337
[c]Inoculum = $1 \times 10^4$ to $4 \times 10^4$ CFU each of $\chi$3456 and $\chi$3337 (equal inocula were given with each experiment)
[d]Geometric mean of CFU from spleens
[e]At 6 days post-inoculation, mice infected with $2 \times 10^3$ CFU of $\chi$3337 alone possessed spleen levels of $2.3 \times 10^5$ CFU of $\chi$3337
[f]Geometric mean of ratio $\chi$3456:$\chi$3337 (P value in 1-tailed Student's t test for ratio > 1:1)
[g]Mean of $\log_{10}$ of ratios ± standard deviation used for statistical analysis Plasmid-cured S. typhimurium were able to multiply in Peyer's patches and reached mesenteric lymph nodes and spleens after p.o. inoculation (FIG. 5, 6, 7). However, differences in the abilities of wild-type versus plasmid-cured S. typhimurium to invade to mesenteric lymph nodes and spleens were consistently found. It was also determined that wild-type S. typhimurium was much more efficient at infecting spleens after p.o. inoculation of mice (wild-type to cured ratios of 1600:1; FIG. 6). However, even cured derivatives reached spleen levels as high as $10^4$ CFU and remained detectable in spleens for as long as 31 days post-inoculation (FIG. 5). After p.o. inoculation with mixtures of wild-type and cured SR-11, significantly higher ratios of wild-type to cured SR-11 were found in spleens and mesenteric lymph nodes as compared with Peyer's patches (FIG. 6).

The i.p. $LD_{50}$'s of plasmid-cured SR-11 and SL1344 were <50 CFU and 400 CFU, respectively, indicating that 100 kb plasmid-cured S. typhimurium retained significant virulence by this route of inoculation (Table 11). It is important to note that neither cured strain hybridized with $^{32}$P-labeled virulence plasmid, so the presence of a chromosomally integrated copy of the plasmid which could contribute to virulence was ruled out. The abilities of wild-type and cured strains to infect spleens after i.v. inoculation was investigated and significant differences in CFU in spleens one week after i.v. inoculation with mixtures of wild-type and cured S. typhimurium (mean wild-type to cured ratios of 7.5:1 and 20:1) were found. The differences in spleen CFU after i.v. inoculation were not as large as those obtained 5 to 7 days after p.o. inoculation (1600:1-and 210:1-fold). These experiments again demonstrated that plasmid-cured S. typhimurium could reach high levels and multiply in spleens and that the greatest effects of the 100 kb plasmid on pathogenesis are after p.o. inoculation. We hypothesize that 100 kb plasmid-cured *S. typhimurium* retains virulence by the i.p. route because the bacteria rapidly multiply extracellularly and are not effeciently phagocytosed in the peritoneal cavity; hence an overwhelming infection develops before mice can check the infection by clearing bacteria to macrophages. When administered by the p.o. route, all or most of the invading bacteria are presumed to be intracellular upon reaching the mesenteric lymph nodes.

What is claimed is:

1. A vaccine for the immunization of a vertebrate or invertebrate comprising a live avirulent bacterium selected from the group consisting of Salmonella, Escherichia and Salmonella-Escherichia hybrids obtained from a pathogenic strain of said bacterium, said pathogenic strain of said bacterium containing a gene encoding adenylate cyclase and a gene encoding cyclic AMP receptor protein and said strain of said bacterium made avirulent by an inactivating mutation in the gene encoding adenylate cyclase and an inactivating mutation in said gene encoding cyclic AMP receptor protein, and wherein upon administration with a pharmaceutically acceptable carrier to said vertebrate or invertebrate, said live avirulent bacteria is effective in evoking an immune response in said vertebrate or invertebrate to immunize against said pathogenic strain.

2. The vaccine according to claim 1 wherein said bacterium is *Salmonella typhimurium*.

3. A vaccine for the immunization of a vertebrate or invertebrate comprising a live avirulent bacterium selected from the group consisting of Salmonella, Escherichia, and Salmonella-Escherichia hybrids obtained from a pathogenic strain of said bacterium that contains a gene encoding adenylate cyclase and a gene encoding cyclic AMP receptor protein, said pathogenic strain of said bacterium made avirulent by an inactivating mutation in the gene encoding adenylate cyclase and in the gene encoding cyclic AMP receptor protein, and wherein said strain of said bacterium also expresses a heterologous gene from a pathogenic microorganism to said vertebrate or invertebrate to produce an antigen wherein upon administration with a pharmaceutically acceptable carrier said vaccine effects an immune response in said vertebrate or invertebrate against said pathogenic microorganism.

4. The vaccine according to claim 3 wherein said bacterium is *Salmonella typhimurium*.

5. The vaccine according to claim 3 wherein said pathogenic microorganism is selected from the group consisting of viruses, bacteria, protozoa, parasites and fungi.

6. The vaccine according to claim 5 wherein said pathogenic microorganism is a bacterium selected from the group consisting of *Neisseria gonorrhoeae, Chlamydia trachomatis, Streptococcus mutans, Mycobacterium tuberculosis, Mycobacterium leprae, Streptococcus pneumoniae, Streptococcus pyogenes, Treponema palladium, Neisseria meningitidis, Mycoplasma pneumoniae, Hemophilus influenzae, Bordetella pertussis, Bordetella avium, Escherichia coli,* and *Streptococcus equi.*

7. A method for stimulating the immune system in a vertebrate or invertebrate, comprising the step of:
administering to said vertebrate or invertebrate an amount of a live avirulent bacterium selected from the group consisting of Salmonella. Escherichia, and Salmonella-Escherichia hybrids obtained from a pathogenic strain of said bacterium, said pathogenic strain of said bacterium containing a gene encoding adenylate cyclase and a gene encoding cyclic AMP receptor protein and said strain of said bacterium made avirulent by an inactivating mutation in the gene encoding adenylate cyclase and an inactivating mutation in said gene encoding cyclic AMP receptor protein which effective in evoking an immune response in said vertebrate or invertebrate to immunize against said pathogenic strain.

8. (Twice amended) The method according to claim 7 wherein said bacterium is *Salmonella typhimurium*.

9. The method according to claim 7 wherein said administrating is accomplished by the introduction of the vaccine by means of oral ingestion, gastric intubation, aerosols, intravenous, intramuscular, subcutaneous, intramammary, intrapenial or intravaginal injection.

10. A live avirulent Salmonella, Escherichia, or Salmonella-Escherichia hybrid which contains a gene encoding adenylate cyclase and a gene encoding cyclic AMP receptor protein, said Salmonella, Escherichia, or Salmonella-Escherichia hybrid made avirulent by an inactivating mutation in a gene encoding adenylate cyclase and an inactivating mutation in a gene encoding cyclic AMP receptor protein.

11. The vaccine according to claim 2 wherein said bacterium is a strain selected from the group χ4062 (ATCC 53647), and χ4064 (ATCC 53648; or a strain retaining the vaccine properties of ATCC 53647 and ATCC 53648.

* * * * *

UNITED STATES PATENT AND TRADEMARK OFFICE
CERTIFICATE OF CORRECTION

PATENT NO. : 5,389,368
DATED : February 14, 1995
INVENTOR(S) : Roy Curtiss III

It is certified that error appears in the above-indentified patent and that said Letters Patent is hereby corrected as shown below:

Title page  left column, line 2, delete "Gurtiss, III" and substitute therefor the correct inventor's name, --Curtiss, III--.

Title page  left column, line 5, delete "Roy Gurtiss, III" and substitute therefor the correct inventor's name, --Roy Curtiss, III--.

Signed and Sealed this

Fourth Day of June, 1996

*Attest:*

BRUCE LEHMAN

*Attesting Officer*  *Commissioner of Patents and Trademarks*